United States Patent
Shi et al.

(10) Patent No.: US 10,400,179 B2
(45) Date of Patent: Sep. 3, 2019

(54) OLEFIN OXIDATION PROCESS, REACTION APPARATUS AND SYSTEM

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Chunfeng Shi, Beijing (CN); Jun Long, Beijing (CN); Bin Zhu, Beijing (CN); Min Lin, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 0 days.

(21) Appl. No.: 15/515,187

(22) PCT Filed: Sep. 29, 2015

(86) PCT No.: PCT/CN2015/000671
§ 371 (c)(1),
(2) Date: Mar. 29, 2017

(87) PCT Pub. No.: WO2016/050004
PCT Pub. Date: Apr. 7, 2016

(65) Prior Publication Data
US 2017/0226429 A1 Aug. 10, 2017

(30) Foreign Application Priority Data
Sep. 29, 2014 (CN) .......................... 2014 1 0513479

(51) Int. Cl.
*B01J 8/02* (2006.01)
*B01J 8/04* (2006.01)
(Continued)

(52) U.S. Cl.
CPC ......... *C10G 29/04* (2013.01); *B01D 53/0423* (2013.01); *B01J 19/00* (2013.01);
(Continued)

(58) Field of Classification Search
CPC ........ C10G 29/00; C10G 29/04; B01D 53/00; B01D 53/02; B01D 53/04; B01D 53/0407;
(Continued)

(56) References Cited

U.S. PATENT DOCUMENTS 5,425,924 A * 6/1995 Finley .................... B01J 8/008
422/176
5,849,937 A 12/1998 Jubin, Jr. et al.
(Continued)

FOREIGN PATENT DOCUMENTS

AU 2006328677 A2 7/2008
CA 2440027 C 5/2010
(Continued)

OTHER PUBLICATIONS

A. Corma et al., Synthesis of an Ultralarge Pore Titanium Silicate Isomorphous to MCM-41 and its Application as a Catalyst for Selective Oxidation of Hydrocarbons, 1994, J. Chem. Soc., Chem. Commun., 147-148. (Year: 1994).*
(Continued)

*Primary Examiner* — Natasha E Young
(74) *Attorney, Agent, or Firm* — Novick, Kim & Lee, PLLC; Allen Xue

(57) ABSTRACT

This invention discloses an olefin oxidation process, including a step of under olefin oxidation conditions, successively
(Continued)

passing a reaction feed from the No.1 catalyst bed through the No.n catalyst bed, wherein if the apparent velocity of each of the reaction materials passing from the No.1 catalyst bed through the No.n catalyst bed is respectively named as $v_1$ to $v_n$, and if m represents any integer in the region [2, n], the relationship $v_{m-1} < v_m$ holds. The process according to this invention is capable of extending the service life of the catalyst, especially the single-pass service life thereof, and at the same time, suppressing any side-reaction over a prolonged period of time. This invention further discloses a fixed-bed reaction apparatus and a system for olefin oxidation.

20 Claims, 9 Drawing Sheets

(51) Int. Cl.

| | |
|---|---|
| B01J 19/24 | (2006.01) |
| B01J 20/02 | (2006.01) |
| B01J 20/04 | (2006.01) |
| B01J 20/32 | (2006.01) |
| B01J 21/04 | (2006.01) |
| B01J 21/06 | (2006.01) |
| B01J 35/00 | (2006.01) |
| C07C 29/48 | (2006.01) |
| C10G 29/04 | (2006.01) |
| B01D 53/04 | (2006.01) |
| C07D 301/12 | (2006.01) |
| C07D 301/19 | (2006.01) |
| C07D 303/04 | (2006.01) |
| B01J 19/00 | (2006.01) |

(52) U.S. Cl.
CPC ............... *B01J 20/02* (2013.01); *B01J 20/04* (2013.01); *B01J 20/041* (2013.01); *B01J 20/3204* (2013.01); *B01J 21/04* (2013.01); *B01J 21/06* (2013.01); *B01J 35/0006* (2013.01); *C07C 29/48* (2013.01); *C07D 301/12* (2013.01); *C07D 301/19* (2013.01); *C07D 303/04* (2013.01); *B01J 2208/025* (2013.01)

(58) Field of Classification Search
CPC . B01D 53/0423; B01J 8/00; B01J 8/02; B01J 8/04; B01J 19/00; B01J 19/24; B01J 20/00; B01J 20/02; B01J 20/04; B01J 20/041; B01J 20/32–3204; B01J 21/00; B01J 21/02; B01J 21/04; B01J 21/06; B01J 35/00; B01J 35/0006; B01J 2208/02; B01J 2208/023–025; C07C 29/00; C07C 29/48; C07D 301/00–03; C07D 301/12; C07D 301/19; C07D 303/00–04

See application file for complete search history.

(56) References Cited

U.S. PATENT DOCUMENTS

| | | | | |
|---|---|---|---|---|
| 6,337,412 | B1* | 1/2002 | Gelbein | B01D 3/009 203/38 |
| 6,475,465 | B2* | 11/2002 | Lin | C01B 37/005 423/326 |
| 7,422,904 | B2* | 9/2008 | Garton | B01J 8/02 422/110 |
| 2003/0097009 | A1 | 5/2003 | Oku et al. | |

FOREIGN PATENT DOCUMENTS

| | | | | |
|---|---|---|---|---|
| CN | 1301599 | A * | 7/2001 | ........... C01B 37/005 |
| CN | 1494535 | A | 5/2004 | |
| CN | 1541212 | A | 10/2004 | |
| CN | 2759585 | Y | 2/2006 | |
| CN | 101274922 | A | 10/2008 | |
| CN | 101279959 | A | 10/2008 | |
| CN | 101314596 | A | 12/2008 | |
| CN | 101397282 | A | 4/2009 | |
| CN | 101885711 | A | 11/2010 | |
| CN | 103586069 | A | 2/2014 | |
| IN | 200500708 | P4 | 4/2007 | |
| RU | 2332409 | C2 | 8/2008 | |
| WO | 0170713 | A1 | 9/2001 | |
| WO | 2002085874 | A1 | 10/2002 | |
| WO | 2002085876 | A1 | 10/2002 | |
| WO | 2003016296 | A3 | 2/2003 | |
| WO | 2004013116 | A1 | 2/2004 | |

OTHER PUBLICATIONS

Takashi Tatsumi et al., "Synthesis of Ti-beta Zeolite with High Oxidation Activity by a Dry-gel Conversion Technique", Chemistry Letters, 1997, pp. 677-678 (Year: 1997).*
Eurpean Patent Office, "Supplementary European Search Report" for EP 15845790, dated Feb. 22, 2018.
Russian Patent Office, Search report for counterpart application RU 2017114007, dated Jan. 28, 2019.
Chinese Patent Office, the First Office Action for CN 201580047702.8 dated Jan. 4, 2019.
Tao, Jialin et al., "Cyclohexane Oxidation Catalyzed by Titanium Silicalite (TS-1) with Hydrogen Peroxide" Journal of Natural Gas Chemistry, vol. 10 No. 4, 2001, pp. 295-349 (Chinese abstract translation on the last page).
Takashi Tatsumi et al., "Synthesis of Ti-beta Zeolite with High Oxidation Activity by a Dry-gel Conversion Technique", Chemistry Letters, 1997, pp. 677-678.
A. Corma et al., "Synthesis of an Ultralarge Pore Titanium Silicate Isomorphous to MCM-41 and its Application as a Catalyst for Selective Oxidation of Hydrocarbons", J. Chem. Soc., Chem. Commun., 1994, pp. 147-148.

* cited by examiner

OLEFIN OXIDATION PROCESS, REACTION APPARATUS AND SYSTEM

The application is a national stage application of PCT/CN2015/000671, published as WO 2016/050004, and filed on Sep. 29, 2015, which claims priority to Chinese Patent Application Serial No. 201410513479.9, file on Sep. 29, 2014, the content of which is incorporated herein by reference in its entirety.

TECHNICAL FIELD

This invention relates to an olefin oxidation process, especially to a process for producing epoxides by olefin catalytic oxidation. This invention further relates to a fixed-bed reaction apparatus and a system for olefin oxidation.

BACKGROUND ART

Epoxides, for example propylene oxide, have been identified as one of the key oxygen-containing organic compounds. As the process for producing propylene oxide, a process by propylene oxidation in the presence of a catalyst (especially a titanium silicalite) to produce propylene oxide has been commercially available.

However, an olefin catalytic oxidation process of this kind is commonly suffering from a problem as, when the reaction apparatus therefor runs for a period of time, both the activity and the selectivity of the catalyst to the aimed oxidation will decrease, that is, the catalyst will gradually lost its activity during use. At present, it is a common skill to regenerate the spent catalyst. However, this regeneration will result in an increase in the running cost of the apparatus and a decrease in the effectiveness thereof. Further, the regenerated catalyst, when reused, needs a long duration for its activity and selectivity to reach a stable state; and at the same time, operations like increasing the reaction temperature are rendered necessary for a stable reaction, which in turn shortens the service life of the catalyst and lowers its selectivity.

Further, an olefin catalytic oxidation process of this kind commonly suffers a problem as, when the reaction apparatus therefor runs for a period of time, the selectivity of the catalyst to side-reactions will increase, resulting in an increase in the percentage of by-products in the reaction discharge, which necessarily complicates the follow-up separation and purification.

Therefore, there remain needs by the prior art olefin catalytic oxidation process for extending the service life of the catalyst, especially the single-pass service life thereof, and at the same time, suppressing any side-reaction over a prolonged period of time.

INVENTION SUMMARY

This invention aims at providing an olefin oxidation process, which is capable of solving the problems in association with the prior art olefin catalytic oxidation process, and characterized by extending the service life of the catalyst, especially the single-pass service life thereof, and at the same time, suppressing any side-reaction over a prolonged period of time.

Specifically, this invention relates to the following aspects.

1. An olefin oxidation process, including a step of under olefin oxidation conditions, successively passing a reaction feed comprising an olefin (preferably at least one out of $C_{3-6}$ α-olefins, more preferably at least one out of propylene and butene, further preferably propylene) and at least one oxidant (preferably at least one out of hydrogen peroxide, organic peroxides and peracids, more preferably hydrogen peroxide) from a No.1 catalyst bed through a No.n catalyst bed (herein, n represents 2, 3, 4, 5, 6, 7, 8, 9, 10, 11, 12, 13, 14, 15, 16, 17, 18, 19 or 20, preferably 2, 3, 4, 5, 6, 7, 8, 9 or 10, more preferably 2, 3, 4 or 5), characterized in that if the apparent velocity of each of the reaction materials passing from the No.1 catalyst bed through the No.n catalyst bed is respectively named as $v_1$ to $v_n$, and if m represents any integer in the region [2, n], the following relationship holds, $v_{m-1} < v_m$, preferably $v_m/v_{m-1} = 1.5$ to 15, more preferably $v_m/v_{m-1} = 2$ to 10, further preferably $v_m v_{m-1} = 2$ to 5.

2. The process according to any one of preceding aspects, wherein if m represents any integer in the region [2, n], the following relationship holds,
$A_{m-1}/A_m > 1$, preferably $A_{m-1}/A_m \geq 1.5$, more preferably $A_{m-1}/A_m \geq 2$, preferably $A_{m-1}/A_m \leq 15$, more preferably $A_{m-1}/A_m \leq 10$, further preferably $A_{m-1}/A_m \leq 5$,
wherein $A_{m-1}$ represents the averaged cross-sectional area of the No. m−1 catalyst bed, $A_m$ represents the averaged cross-sectional area of the No. m catalyst bed.

3. The process according to any one of preceding aspects, obtaining a reaction discharge comprising an olefin oxide, which further comprises a step of isolating the olefin oxide from the reaction discharge to leave over an exhaust stream.

4. The process according to any one of preceding aspects, wherein there is a compartment between any two or more pairs of adjacent catalyst beds among the No.1 catalyst bed through the No.n catalyst bed, and a carrier fluid is introduced into the compartment and is at least one out of the reaction discharge, a solvent, an inert gas and the exhaust stream, more preferably at least one out of the reaction discharge and the inert gas.

5. The process according to any one of preceding aspects, wherein the No.1 catalyst bed through the No.n catalyst bed is each respectively loaded with at least one titanium silicalite.

6. The process according to any one of preceding aspects, wherein in the reaction feed, the ratio by molar of the olefin to the at least one oxidant is 0.1-10:1, preferably 0.2-5:1, based on the total amount of the catalyst loaded in the No.1 catalyst bed through the No.n catalyst bed, the weight hourly space velocity of the olefin is 0.1-20 $h^{-1}$, preferably 0.2-10 $h^{-1}$, and the olefin oxidation conditions include: a reaction pressure (gauge) of 0-5 MPa, preferably 0.1-3.5 MPa, and a reaction temperature of 0-120 degrees Celsius, preferably 20-80 degrees Celsius (for example 30-60 degrees Celsius).

7. The process according to any one of preceding aspects, wherein if m represents any integer in the region [2, n], the following relationship holds,
$T_{m-1} - T_m = 5$ to 30, preferably $T_{m-1} - T_m = 10$ to 20, wherein $T_{m-1}$ represents the reaction temperature (in degree Celsius) across the No. m−1 catalyst bed, $T_m$ represents the reaction temperature (in degree Celsius) across the No. m catalyst bed.

8. A fixed-bed reaction apparatus, including an entrance (1), a reaction zone (3) and an exit (2), wherein within the reaction zone (3), there are arranged the No.1 catalyst bed through the No.n catalyst bed (herein, n represents 2, 3, 4, 5, 6, 7, 8, 9, 10, 11, 12, 13, 14, 15, 16, 17, 18, 19 or 20, preferably 2 or 3), and wherein a reaction feed enters the reaction zone (3) via the entrance (1), successively passes from the No.1 catalyst bed through the No.n catalyst bed, then flows out of the exit (2) as the reaction discharge, characterized in that the fixed-bed reaction apparatus further comprises a speed-increasing means, if the apparent velocity of each of the reaction materials passing from the No.1 catalyst bed through the No.n catalyst bed is respectively named as $v_1$ to $v_n$, and if m represents any integer in the region [2, n], the speed-increasing means is designed so that the following relationship holds, $v_{m-1} < v_m$, preferably $v_m/v_{m-1}$=1.5 to 15, more preferably $v_m/v_{m-1}$=2 to 10, further preferably $v_m/v_{m-1}$=2 to 5.

9. The fixed-bed reaction apparatus according to any one of preceding aspects, wherein the speed-increasing means is a diameter-changing section of the reaction zone (3) and/or an internal arranged within the reaction zone (3), and the diameter-changing section or the internal is so arranged that if m represents any integer in the region [2, n], the following relationship holds, $A_{m-1}/A_m > 1$, preferably $A_{m-1}/A_m \geq 1.5$, more preferably $A_{m-1}/A_m \geq 2$, preferably $A_{m-1}/A_m \leq 15$, more preferably $A_{m-1}/A_m \leq 10$, further preferably $A_{m-1}/A_m \leq 5$, wherein $A_{m-1}$ represents the averaged cross-sectional area of the No. m−1 catalyst bed, $A_m$ represents the averaged cross-sectional area of the No. m catalyst bed.

10. The fixed-bed reaction apparatus according to any one of preceding aspects, wherein the speed-increasing means is a reaction discharge introduction conduit, a solvent introduction conduit, an inert gas introduction conduit or any combination thereof, wherein the reaction discharge introduction conduit is arranged to introduce a part of the reaction discharge into a compartment between any two or more pairs of adjacent catalyst beds among the No.1 catalyst bed through the No.n catalyst bed, the solvent introduction conduit is arranged to introduce a solvent into a compartment between any two or more pairs of adjacent catalyst beds among the No.1 catalyst bed through the No.n catalyst bed, and the inert gas introduction conduit is arranged to introduce an inert gas into a compartment between any two or more pairs of adjacent catalyst beds among the No.1 catalyst bed through the No.n catalyst bed.

11. A system for olefin oxidation, comprising at least a reaction feed unit, an olefin oxidation reaction unit and a reaction discharge separation unit, wherein the olefin oxidation reaction unit comprises one or more of the fixed-bed reaction apparatus according to any one of preceding aspects.

12. The system according to any one of preceding aspects, wherein the reaction discharge separation unit isolates an olefin oxide from the reaction discharge of the fixed-bed reaction apparatus to leave over an exhaust stream, and wherein the speed-increasing means is an exhaust stream introduction conduit, which is arranged to introduce the exhaust stream or a part thereof into a compartment between any two or more pairs of adjacent catalyst beds among the No.1 catalyst bed through the No.n catalyst bed.

TECHNICAL EFFECTS

According to the olefin oxidation process of this invention, it is capable of effectively extending the service life of the catalyst, especially the single-pass service life thereof, lowering the frequency of catalyst regeneration, which necessarily improves the production effectiveness, and at the same time, the production stability, which leads to elongation in the total service life of the catalyst.

According to the olefin oxidation process of this invention, even after an elongated period of continuous run, the oxidant conversion maintains at a substantially stable level, and the oxidant utilization rate and the selectivity to the aimed epoxide product maintain at a relatively higher level. Especially, even after an elongated period of continuous run, the selectivity to the aimed epoxide product maintains at a relatively higher level, while the selectivity to by-products at a relatively lower level, which will simplify the follow-up separation and purification.

FIGURE DESCRIPTION

Figure 1:
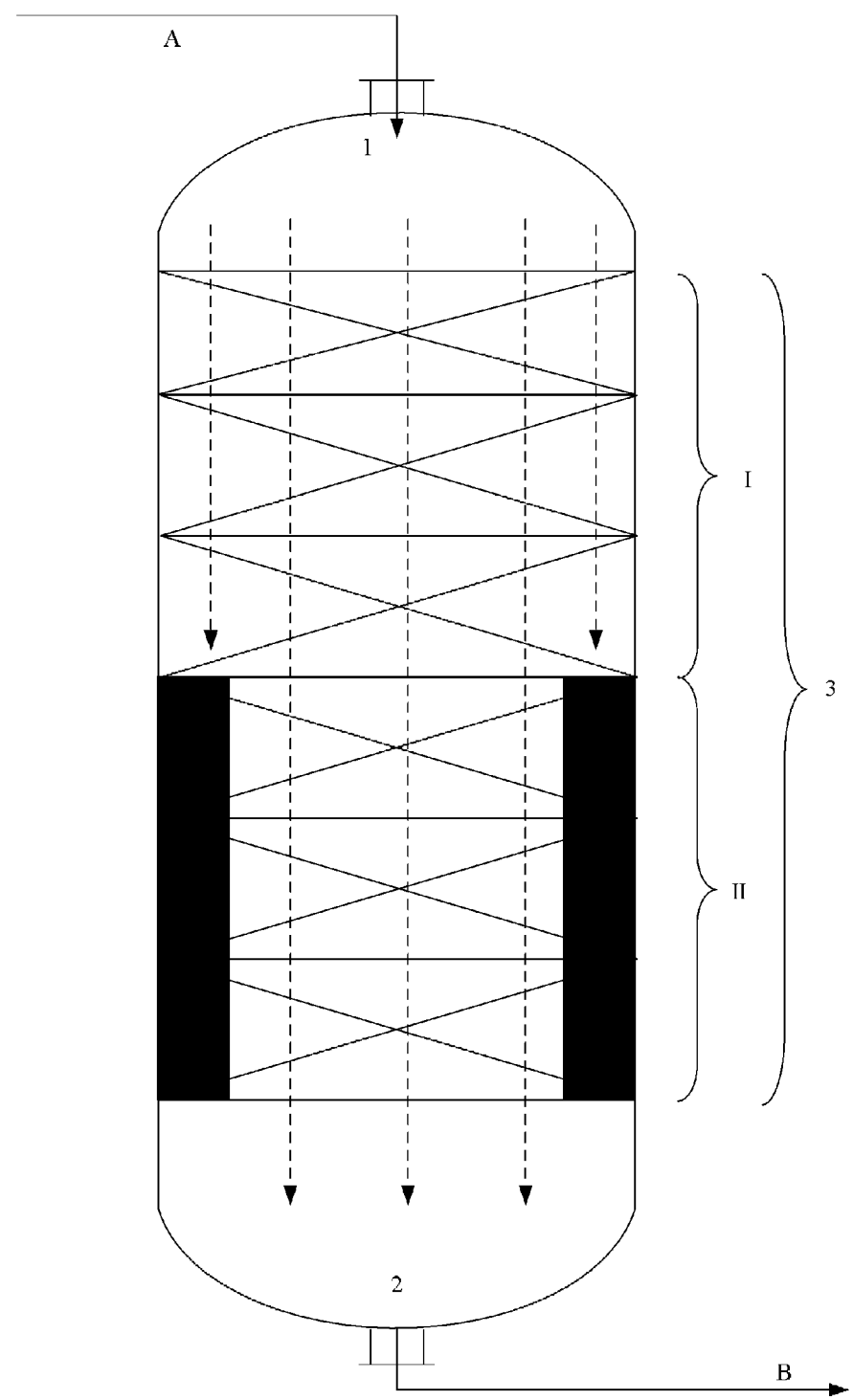
FIGS. 1 to 6 illustrate some embodiments of the reactor internal.
Figure 2:
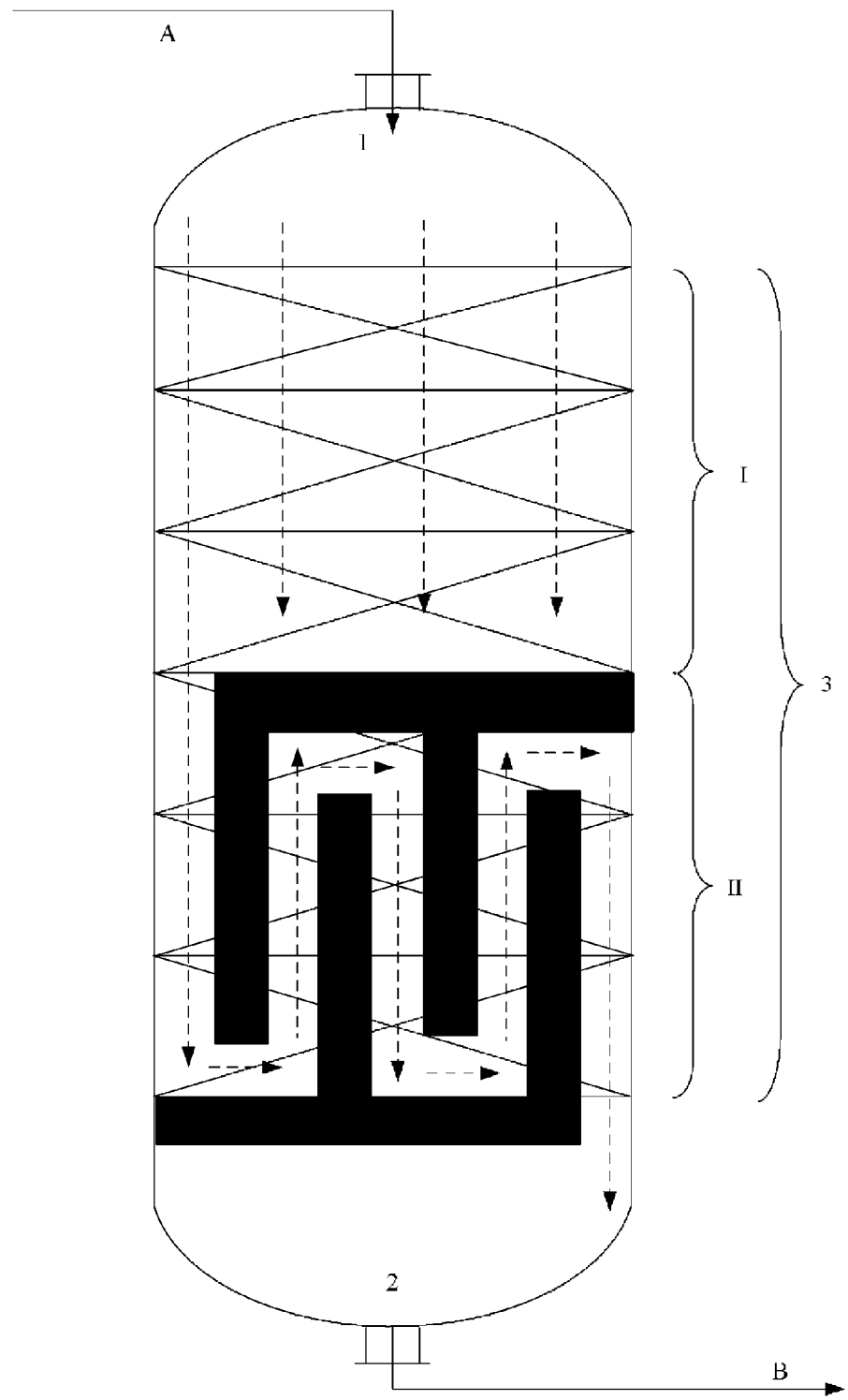
Figure 3:
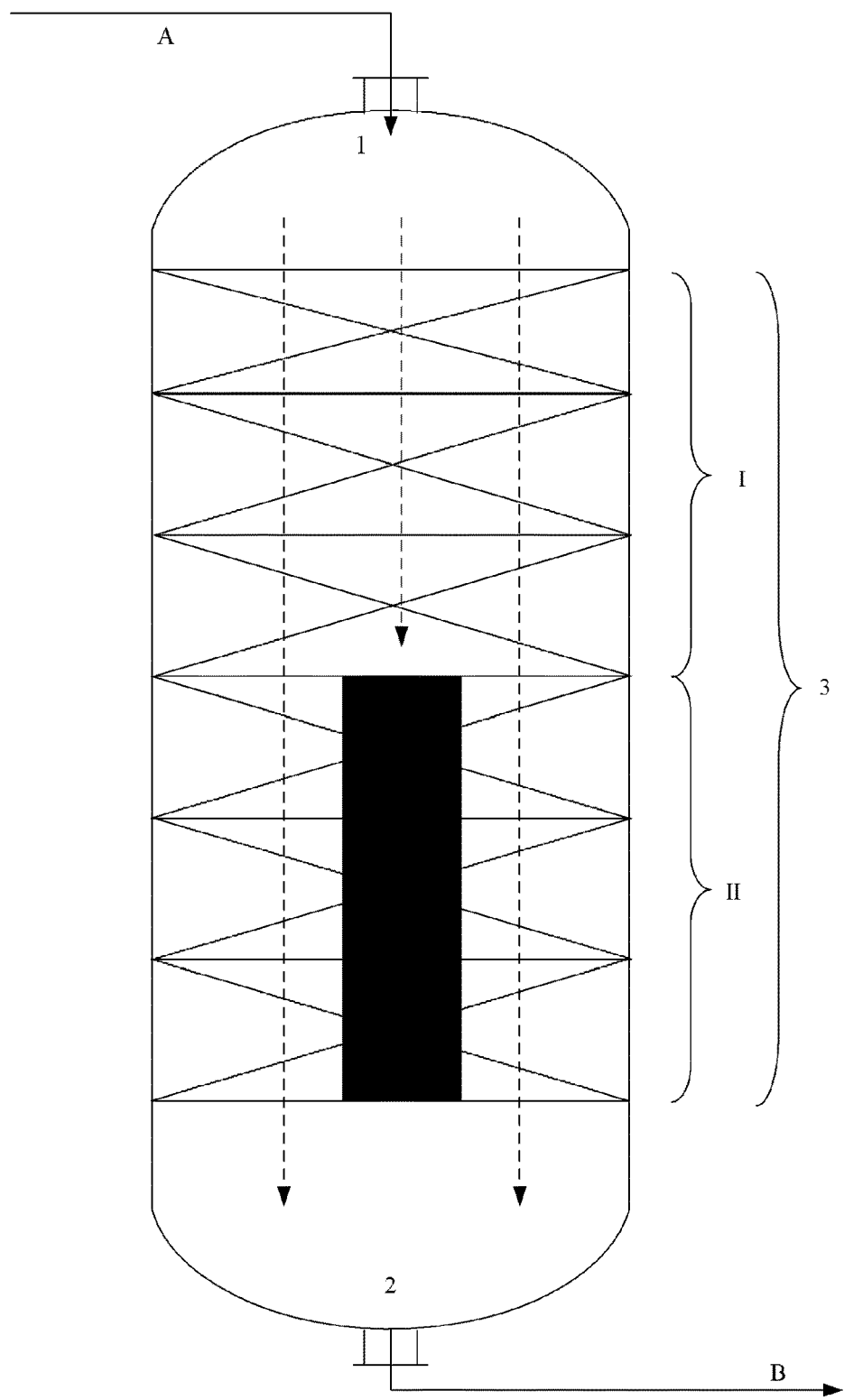
Figure 4:
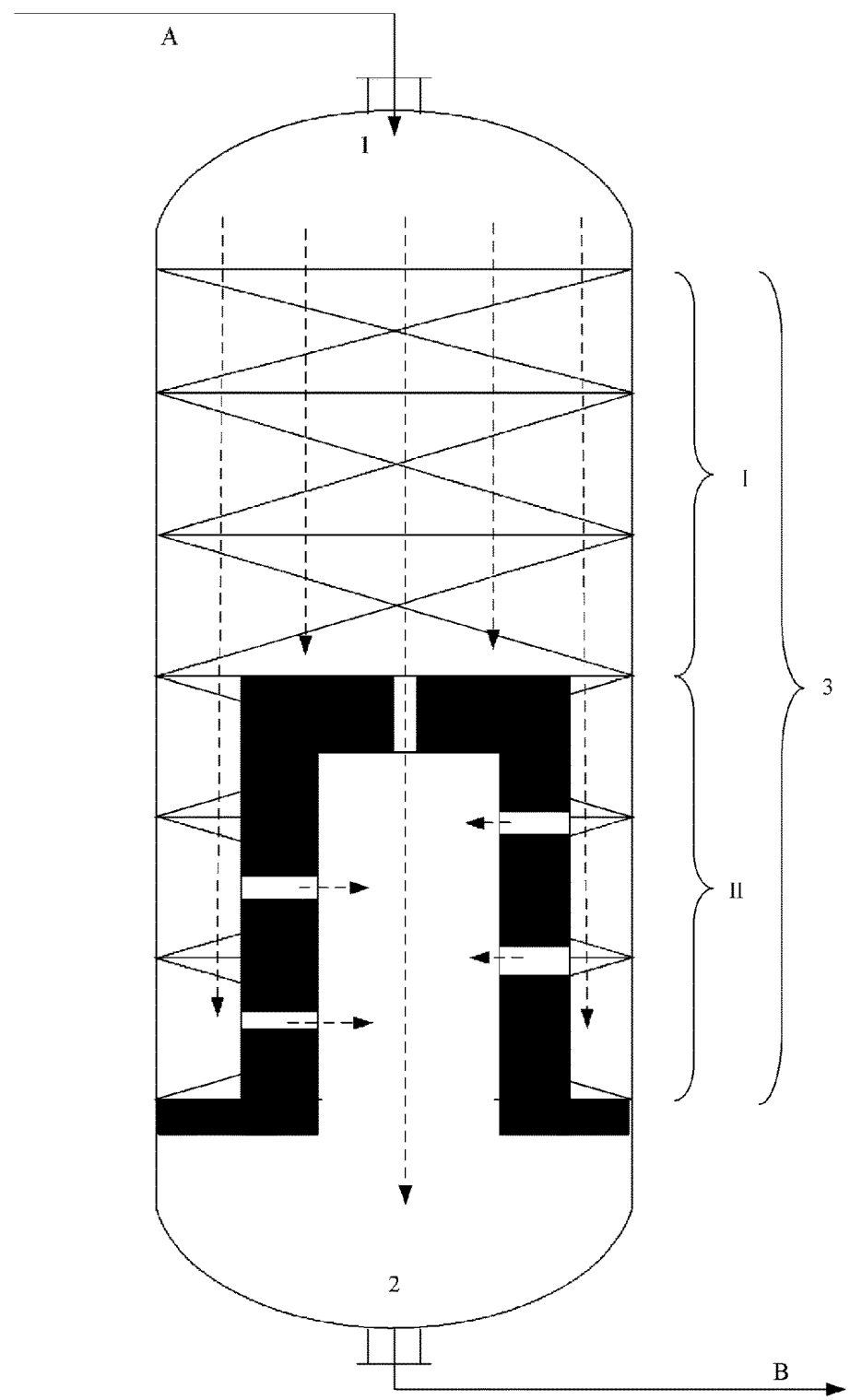
Figure 5:
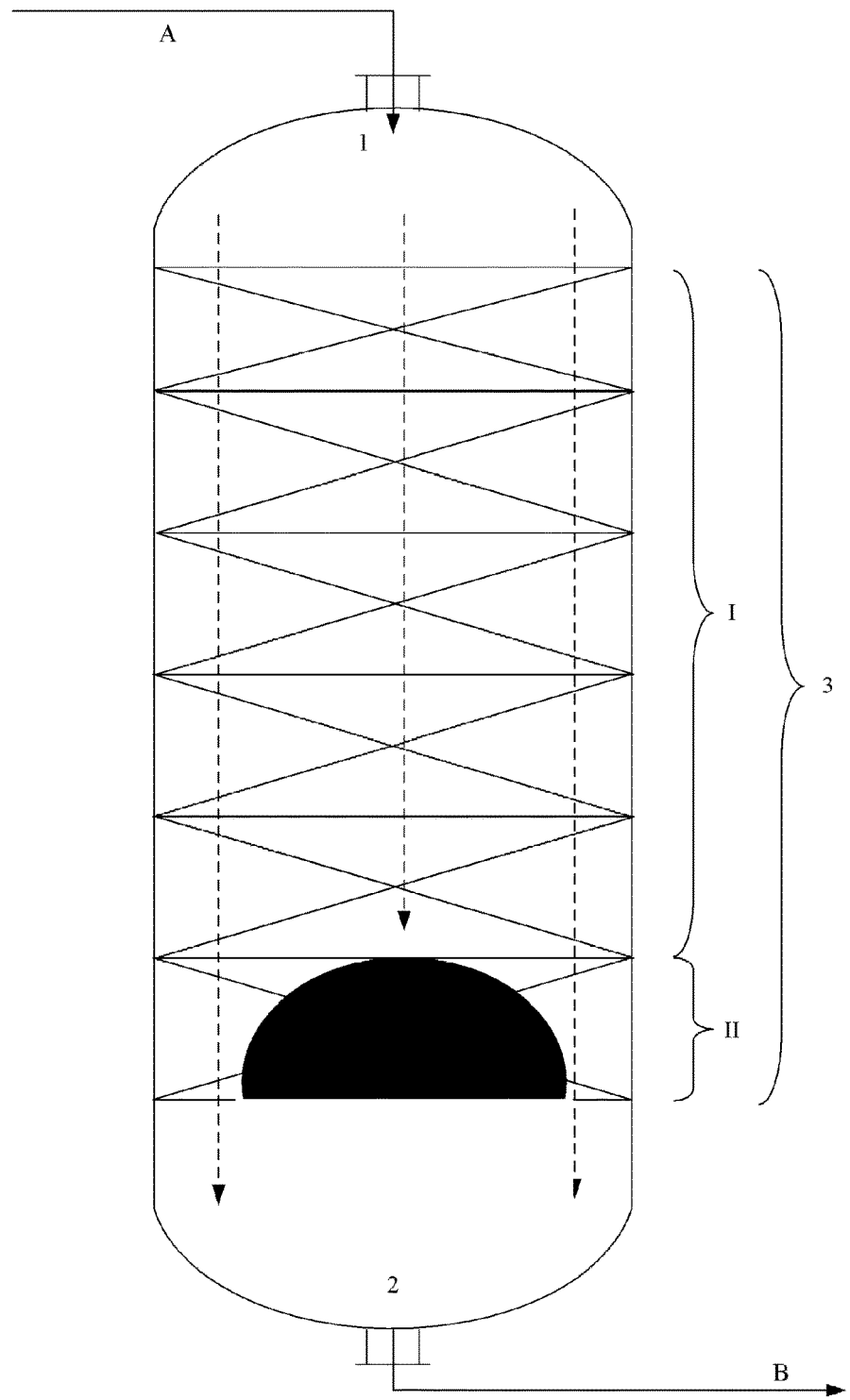
Figure 6:
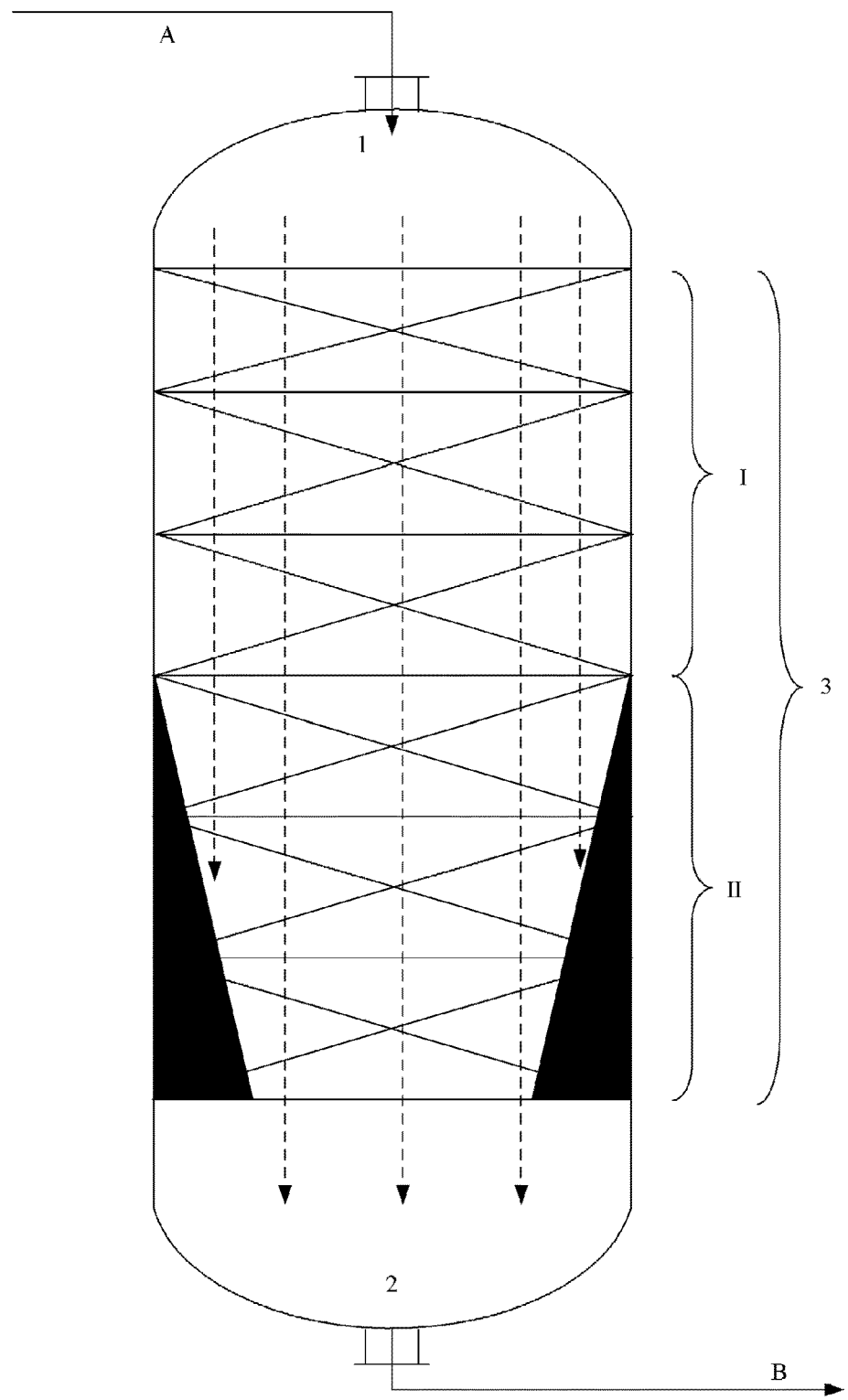

In the figures, the reference symbol 1 denotes the entrance, the reference symbol 2 denotes the exit, the reference symbol I denotes the No.1 catalyst bed, the reference symbol II denotes the No.2 catalyst bed, the reference symbol III denotes the No.3 catalyst bed, the blank space between different catalyst beds denotes the compartment, the reference symbol 3 denotes the reaction zone, the reference symbol A denotes the reaction feed, the reference symbol B denotes the reaction discharge, the reference symbols B1 to B4 denote the reaction discharge introduction conduit, the reference symbol C denotes the exhaust stream, the solvent or the inert gas, the reference symbols C1 to C4 denote the exhaust stream introduction conduit, the solvent introduction conduit or the inert gas introduction conduit, the dashed lines with an arrow head denote the direction in which the reaction material flows, the solid color filled area at the portion where the No.2 catalyst bed II locates in each of the FIGS. 1 to 6 denotes the reactor internal, which has a vertical section as illustrated in each figure.

For simplified description, in the context of this specification and the figures, as an example, the reaction material flows from up to down, the reaction zone 3 is 1 in number, the catalyst bed is 2 or 3 in number, the entrance and the exit of the reaction apparatus are both 1 in number, the introduction conduit are 4 in number, and so on, however, this invention is not limited thereto.

SPECIFIC MODE TO CARRY OUT THIS INVENTION

This invention will be described in details hereinafter with reference to the following specific embodiments. However, it should be noted that the protection scope of this invention should not be construed as limited to these specific embodiments, but rather determined by the attached claims.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

Further, to the extent that any meaning or definition of a term in this document conflicts with any meaning or definition of the same term in a document incorporated by reference, the meaning or definition assigned to that term in this document shall govern.

Unless otherwise specified, percents, parts or ratios or the like mentioned in this specification are all on a weight basis.

In the context of this specification, "at least one" refers to one or more (for example two or more).

According to this invention, an olefin oxidation process is provided, which includes a step of under olefin oxidation conditions, successively passing a reaction feed from a No.1 catalyst bed through a No.n catalyst bed.

According to this invention, n represents an integer in the range of from 2 to 50, preferably 2, 3, 4, 5, 6, 7, 8, 9, 10, 11, 12, 13, 14, 15, 16, 17, 18, 19 or 20, more preferably 2, 3, 4, 5, 6, 7, 8, 9 or 10, more preferably 2, 3, 4 or 5, for example 2.

According to this invention, if the apparent velocity of each of the reaction materials passing from the No.1 catalyst bed through the No.n catalyst bed is respectively named as $v_1$ to $v_n$, and if m represents any integer in the region [2, n], the relationship $v_{m-1} < v_m$ holds.

In the context of this specification, by "m represents any integer in the region [2, n]", means that m represents any one integer in the range of from 2 to n, or in other words, is any one selected from the range consisting of 2, 3, . . . , n, and when n=2, m=2.

According to this invention, the wording "successively passing the reaction feed from the No.1 catalyst bed through the No.n catalyst bed" means that the continuous and successive passage from the No.1 catalyst bed through the No.n catalyst bed constitutes a pathway along which the reaction feed flows, however, this does not mean that the reaction feed passes from the No.1 catalyst bed through the No.n catalyst bed without any change. In fact, immediately after entering the No.1 catalyst bed, the reaction feed will change (for example in terms of its composition or properties) due to e.g. an olefin oxidation reaction, whereby being rendered different from its original composition or properties as the reaction starting material. In this connection, to be consistent with the common understanding of a person skilled in the art on the term "reaction starting material", in the context of this specification, the reaction feed that is passing through each catalyst bed is generally referred to as reaction material. Further, when passing through different catalyst beds, the reaction material will change due to various reasons (for example by conducting a reaction or being introduced therein a new material like a carrier fluid), and for these reasons, reaction materials passing through different catalyst beds are generally different from each other (for example in terms of its composition or properties). This invention focuses on the apparent velocity of each reaction material when passing through the corresponding catalyst bed.

According to this invention, the reaction feed or the reaction material generally presents in the form of liquid mixture or gas-liquid mixture, but not limiting thereto.

In the context of this specification, the apparent velocity (with a unit of kg/(m$^2$·s)) refers to the ratio of the flow rate by mass per unit time (with a unit of kg/s) of a reaction material past through the whole length of a specific catalyst bed to a cross-sectional area (with a unit of m$^2$) of the specific catalyst bed. For example, the apparent velocity of the reaction material passing through the No.1 catalyst bed is named as $v_1$, which refers to the ratio of the flow rate by mass per unit time (with a unit of kg/s) of the reaction material past through the whole length of the No.1 catalyst bed to a cross-sectional area (with a unit of m$^2$) of the No.1 catalyst bed. Herein, to simplify the description of the present invention, the term "cross-sectional area" generally refers to an averaged cross-sectional area. In this connection, by "averaged cross-sectional area", it refers to the ratio of the total volume (with a unit of m$^3$) of the catalyst loaded into a catalyst bed to the length (with a unit of m) of the catalyst bed along the flowing path of or in the flowing direction of the reaction material, which is familiar to a person skilled in the art. For a catalyst bed having a fixed or constant diameter, the averaged cross-sectional area corresponds to the cross-sectional area. Further, the present invention does not intend to specify the apparent velocity (or its absolute value) of the reaction material passing through any catalyst bed, and any value known in this field is applicable as such herein. For example, in general, the apparent velocity (or its absolute value) of the reaction material passing through the No.1 catalyst bed may be in the range of 0.001-200 kg/(m$^2$·s), but sometimes not limiting thereto.

According to this invention, to further improve the effects to be obtained with this invention, it is preferably $v_m/v_{m-1}$=1.5-15, more preferably $v_m/v_{m-1}$=2-10, further preferably $v_m/v_{m-1}$=2-5. For example, when m=2, it is preferably $v_2/v_1$=1.5-15, more preferably $v_2/v_1$=2-10, further preferably $v_2/v_1$=2-5.

According to this invention, the No.1 catalyst bed through the No.n catalyst bed may be arranged into a single one reactor, constituting multiple reaction zones of the reactor, or into n reactors respectively, constituting n multiple reactors, or in any combination thereof into two or multiple (at most n−1) reactors, constituting a combination of multiple reaction zones and multiple reactors.

According to this invention, the No.1 catalyst bed through the No.n catalyst bed may be continuously connected, whereby constituting an integrated catalyst bed, or there may exist a compartment between any two or more pairs of adjacent catalyst beds, whereby constituting a multiple-staged catalyst bed. The compartment may be an internal space of the reactor, and in this case, if needed, into this internal space, one or more of non-catalyst beds (for example, a bed made of an inactive filler as hereafter described) or reactor internals (for example, a fluid distributor, an internal for supporting the catalyst bed, or a heat exchanger or the like) or the like may be introduced, whereby increasing the flexibility of the olefin oxidation reaction of the present invention.

According to this invention, the No.1 catalyst bed through the No.n catalyst bed may be successively connected in series along the flowing path of or in the flowing direction of the reaction feed in an upstream and downstream relationship, wherein the No.1 catalyst bed locates most upstream, the No.n catalyst bed locates most downstream. Nevertheless, some or all of the catalyst beds may be arranged side by side in space, as long as the reaction feed is necessarily made to flow through one after another. According to this invention, the No.1 catalyst bed through the No.n catalyst bed may each independently comprise one or more catalyst bed(s). In the case of comprising more catalyst beds, the more catalyst beds may connect to one another in series or in parallel, or a combination thereof. For example, the more catalyst beds may be divided into multiple groups, different catalyst beds in each group may connect to one another in series and/or in parallel, and the multiple groups may connect to one another in series and/or in parallel.

According to this invention, the No.1 catalyst bed through the No.n catalyst bed may each independently present in a form known in this field, for example, a fluidized bed, an expanded bed, a slurry bed or a fixed-bed, and to facilitate the olefin oxidation reaction of this invention, it is preferably that the No.1 catalyst bed through the No.n catalyst bed are all in the form of fixed-bed.

According to this invention, into the No.1 catalyst bed through the No.n catalyst bed, there may be each independently loaded with at least one catalyst.

According to this invention, as the catalyst, for example there may be exemplified various catalysts known in this field that are suitable for catalyzing olefin oxidation to produce an epoxide, especially titanium silicalites.

According to this invention, the titanium silicalite in general refers to a specific type of zeolite wherein a part of silicon atoms in the crystal lattice skeleton thereof is replaced by titanium atoms, which may be represented by the formula $xTiO_2 \cdot SiO_2$. This invention does not intend to specifically limit the amount of titanium atom in the titanium silicalite, which has been familiar in this field. Specifically, x may be 0.0001-0.05, preferably 0.01-0.03, more preferably 0.015-0.025.

According to this invention, the titanium silicalite may be any one commonly known in this field of various topological structure, for example, the titanium silicalite may be selected from the group consisting of a titanium silicalite of the structure MFI (for example TS-1), a titanium silicalite of the structure MEL (for example TS-2), a titanium silicalite of the structure BEA (for example Ti-Beta), a titanium silicalite of the structure MWW (for example Ti-MCM-22), a titanium silicalite of the structure MOR (for example Ti-MOR), a titanium silicalite of the structure TUN (for example Ti-TUN), a titanium silicalite of the two-dimensional hexagonal structure (for example Ti-MCM-41, Ti-SBA-15), a titanium silicalite of other structures (for example Ti-ZSM-48) or the like. The titanium silicalite is preferably selected from the group consisting of a titanium silicalite of the structure MFI, a titanium silicalite of the structure MEL, a titanium silicalite of the two-dimensional hexagonal structure and a titanium silicalite of the structure BEA, more preferably a titanium silicalite of the structure MFI.

According to this invention, it is preferably that the titanium silicalite is a hollow titanium silicalite, whereby further extending the single-pass service life of the catalyst, and at the same time, improving catalyst performance and oxidant conversion, product selectivity and oxidant utilization. The hollow titanium silicalite may be a titanium silicalite of the structure MFI, whose crystalline grain has a hollow structure having a cavity, whose radial length is 5-300 nm, which has a benzene adsorption capacity of at least 70 mg/g if determined under conditions of 25 degrees Celsius, $P/P_0=0.10$ and an adsorption duration of 1 h. For the titanium silicalite, there is a hysteresis loop between the adsorption isotherm curve and the desorption isotherm curve in the cryogenic nitrogen adsorption determination. The hollow titanium silicalite may be commercially available (for example a molecular sieve named as HTS sold by Hunan Jianchang petrochemical inc.), or may be produced in line with a process disclosed by the Chinese patent CN1132699C.

According to this invention, specifically, the No.1 catalyst bed through the No.n catalyst bed is each independently loaded with at least one of the aforesaid titanium silicalites. In this regard, different catalyst beds may be loaded with different kinds of titanium silicalite or with the same kind of titanium silicalite. Further, each catalyst bed may be loaded with only one of the aforesaid titanium silicalites, or may be loaded with one or more of aforesaid titanium silicalites at any predetermined relative ratio therebetween.

According to this invention, it is preferably that the titanium silicalite loaded into the No.1 catalyst bed is a hollow titanium silicalite, while the titanium silicalite loaded into the No.n catalyst bed is other titanium silicalite than the hollow titanium silicalite, for example one or more selected from the group consisting of a titanium silicalite of the structure MFI (for example TS-1), a titanium silicalite of the two-dimensional hexagonal structure (for example Ti-MCM-41) and a titanium silicalite of the structure BEA (for example Ti-Beta), so as to further postpone deactivation rate of the titanium silicalite. It is more preferably that the titanium silicalite loaded into the No.1 catalyst bed is the hollow titanium silicalite, the titanium silicalite loaded into the No.n catalyst bed is the titanium silicalite TS-1. By doing so, it is possible to further postpone deactivation rate of the titanium silicalite, extend the single-pass service life of the titanium silicalite, and further improve the selectivity to the aimed epoxide product.

According to this invention, the titanium silicalite as aforesaid may be in the form of raw powder, or molded product, preferably in the form of molded product. Molded titanium silicalite generally comprises a titanium silicalite as the active component and a carrier as the binder, wherein the amount of the titanium silicalite may be commonly determined. Generally speaking, based on the total amount of the molded titanium silicalite, the amount of the titanium silicalite may be 5-95 wt %, preferably 10-95 wt %, more preferably 70-90 wt %, the amount of the carrier may be 5-95 wt %, preferably 5-90 wt %, more preferably 10-30 wt %. The carrier for the molded titanium silicalite may be commonly selected, such as alumina and/or silica. The process for producing a molded titanium silicalite is well known in this field, and detailed description thereon is omitted herein. There is no specific limitation on the particle size of the molded titanium silicalite, which may be accordingly determined depending on its shape in practical use. Generally speaking, the averaged particle size of the molded titanium silicalite may be 4-10000 microns, preferably 5-5000 microns, more preferably 40-4000 microns, for example 100-2000 microns. The averaged particle size is on a volume basis and may be determined by a laser particle size analyzer.

According to this invention, the amount by mass of the catalyst (specifically titanium silicalite) loaded into each of the No.1 catalyst bed through the No.n catalyst bed may be the same as one another, or may be different from one another. According to an embodiment of this invention, if m represents any integer in the region [2, n], $W_{m-1}/W_m$ would be 0.1-20, preferably 0.5 or more, more preferably 1 or more, further preferably 2 or more. Herein, $W_{m-1}$ represents the amount of the catalyst loaded into the No. m−1 catalyst bed, and $W_m$ represents the amount of the catalyst loaded into the No. m catalyst bed. $W_{m-1}/W_m$ is preferably 15 or less, more preferably 10 or less. It is further preferably that $W_{m-1}/W_m$ is 2-10:1. If the catalyst presents as a molded titanium silicalite, both $W_{m-1}$ and $W_m$ are determined by the amount of the titanium silicalite in the molded titanium silicalite. Further, the catalyst load for each catalyst bed may be suitably determined as needed (for example according to the production capacity), without any specific limitation thereto herein.

According to this invention, the total amount of the catalyst (especially titanium silicalite), i.e. the total amount of the catalyst loaded into the No.1 catalyst bed through the No.n catalyst bed, may be specifically determined according to the throughput of the system. Generally speaking, the total amount of the catalyst is such that the weight hourly space velocity of olefin (as a component of the reaction feed) reaches 0.1-20 $h^{-1}$, preferably 0.2-10 $h^{-1}$.

According to this invention, in addition to the catalyst, if needed, it is possible to further load an inactive filler into the No.1 catalyst bed through the No.n catalyst bed. It is acceptable to load the inactive filler into each of the No.1 catalyst bed through the No.n catalyst bed respectively, or into one or more of the No.1 catalyst bed through the No.n catalyst bed. By loading into a catalyst bed the inactive filler, it is possible to adjust the amount of the catalyst in said catalyst bed, whereby adjusting the reaction speed. For a specific catalyst bed, if an inactive filler is to be loaded, the amount of the inactive filler may be 5-95 wt %, relative to the total amount of the catalyst and the inactive filler loaded into this specific catalyst bed. Herein, by inactive filler, it refers to a filler having no or substantially no catalytic activity regarding the olefin oxidation reaction, which has been well known in this field, and can be exemplified as but not limiting to: one or more of quartz sand, ceramic ring and ceramic chip.

According to this invention, the reaction feed (herein specifically referring to the reaction material immediately before entering the No.1 catalyst bed) comprises an olefin and an oxidant as the components.

According to this invention, the oxidant may be any agent commonly used to oxidate an olefin. It is preferably that the oxidant is a peroxide. By peroxide, it refers to a compound containing in its molecular structure an —O—O— bond, which may be selected from the group consisting of hydrogen peroxide, organic peroxides and peracids. By organic peroxide, it refers to a compound obtained by replacing one or two hydrogen atom(s) in the molecular of hydrogen peroxide by an organic group. By peracid, it refers to an organic oxyacid containing in its molecular structure an —O—O— bond. The examples of peroxide include but not limit to: hydrogen peroxide, tert-butyl hydroperoxide, dicumyl peroxide, hexyl hydrogen peroxide, peracetic acid and perpropionic acid. It is preferably that, the oxidant is hydrogen peroxide, so as to further reduce the cost rendered by separation. The hydrogen peroxide may present in any form commonly known in this field. As the oxidant, one kind or a mixture of two or more kinds at any ratio therebetween could be used.

According to this invention, the amount of the oxidant to be used may be determined according to the amount of olefin contained in the reaction feed. Generally, in the reaction feed, the ratio by molar of the olefin to the oxidant may be 0.1-10:1, preferably 0.2-5:1.

According to this invention, the reaction feed may further optionally comprise a solvent, for a better control of the reaction speed. This invention does not intend to specify the nature of the solvent, as long as it is a solvent commonly used in an olefin oxidation reaction. It is preferably that the solvent is at least one of water, a $C_1$-$C_{10}$ alcohol, a $C_3$-$C_{10}$ ketone, a $C_2$-$C_{10}$ nitrile and a $C_1$-$C_6$ carboxylic acid. The solvent is preferably one or more of a $C_1$-$C_6$ alcohol, a $C_3$-$C_8$ ketone and a $C_2$-$C_5$ nitrile. It is more preferably that the solvent is one or more of methanol, ethanol, acetonitrile, n-propanol, iso-propanol, tert-butanol, iso-butanol and acetone. The solvent is further preferably one or more of methanol, acetonitrile, acetone and tert-butanol. As the solvent, one kind or a mixture of two or more kinds at any ratio therebetween could be used.

According to this invention, there is no specific limitation on the amount of the solvent, which can be determined depending on the amounts of the olefin and the oxidant. Generally, in the reaction feed, the ratio by molar of the solvent to the olefin may be 1-100:1, preferably 2-80:1.

According to this invention, if needed, the reaction feed may further optionally comprise an alkaline substance, so as to maintain the pH value of the reaction feed at a range of 6.5 to 9. Examples of the alkaline substance include but not limiting to: ammonia (i.e., $NH_3$), amines, quaternary ammonium hydroxide and $M^1(OH)_n$ (wherein $M^1$ is an alkali metal or alkaline earth metal, such as Na, K, Mg or Ca, n is an integer representing the valence of $M^1$). As the alkaline substance, one kind or a mixture of two or more kinds at any ratio therebetween could be used.

According to this invention, the olefin may be at least one of $C_2$-$C_{16}$ α-olefins, preferably at least one of $C_{3-6}$ α-olefins. The olefin may be a mono-olefin or polyene, preferably a mono-olefin. Specifically, the olefin may be at least one of propylene and butene, further preferably propylene. As the olefin, one kind or a mixture of two or more kinds at any ratio therebetween could be used.

According to this invention, the olefin oxidation conditions may be determined according to the aimed epoxide product. Specifically, olefin oxidation conditions in the respective catalyst beds may be the same as or different from one another (preferably the same as one another), and include: a reaction pressure (gauge) of 0-5 MPa, preferably 0.1-3.5 MPa, and a reaction temperature of 0-120 degrees Celsius, preferably 20-80 degrees Celsius (for example 30-60 degrees Celsius).

According to this invention, from the standpoint of obtaining more desirable technical effects, it is preferably that along the path from the No.1 catalyst bed through the No.n catalyst bed, the reaction temperatures gradually decrease. Specifically, if m represents any integer in the region [2, n], $T_{m-1}$ is 5-30 degrees Celsius higher than $T_m$, preferably 10-20 degrees Celsius higher than $T_m$, wherein $T_{m-1}$ represents the reaction temperature (in degree Celsius) in the No. m−1 catalyst bed, $T_m$ represents the reaction temperature (in degree Celsius) in the No. m catalyst bed. For example, when n represents 2, the reaction temperature in the No.2 catalyst bed may be preferably 5-30 degrees Celsius lower than that in the No.1 catalyst bed, more preferably 10-20 degrees Celsius lower. This reduction in temperature may be obtained by contacting the reaction material immediately before entering or that is passing through the No. m catalyst bed with a heat exchange medium to conduct heat exchange, or may be as described hereinafter, by introducing a carrier fluid at a lower temperature into the reaction material immediately before entering the No. m catalyst bed, or a combination of two.

According to this invention, there is no specific limitation on the height of the catalyst bed (or the length of the catalyst bed along the flowing path of or in the flowing direction of the reaction material), but is generally $H_1:H_2: \ldots :H_n$=0.5-5:0.5-5: ... :0.5-5, or $H_1:H_2: \ldots :H_n$=0.8-1.2: 0.8-1.2: ... :0.8-1.2, or $H_1:H_2: \ldots :H_n$=0.95-1.05: 0.95-1.05: ... :0.95-1.05, or all catalyst beds have substantially the same height. Herein, $H_1$ represents the height of the No.1 catalyst bed, $H_2$ represents the height of the No.2 catalyst bed, . . . , $H_n$ represents the height of the No.n catalyst bed.

According to this invention, by the olefin oxidation reactions conducted in the No.1 catalyst bed through the No.n catalyst bed, a reaction discharge comprising an aimed olefin oxide (for example an epoxide) is obtained. Herein, by reaction discharge, it specifically refers to the reaction material immediately after leaving the No.n catalyst bed.

According to this invention, the olefin oxidation process if needed may further comprise a step of isolating the olefin oxide from the reaction discharge, whereby leaving over an exhaust stream. Herein, the exhaust stream may be not subject to a further separation and therefore presents as a mixture composed e.g. of unreacted reactants, by-products and any solvent, or may be further isolated respectively into unreacted reactants, by-products and solvent, both of which may be used as such as the exhaust stream without any further purification. As the separation process, it is possible to use that commonly used in this field for this purpose, there is no specific limitation thereon. Further, the isolated unreacted reactants and solvent (if any) may be recycled as a part of the reaction feed.

According to this invention, various ways can be adopted to meet the requirements of the present invention as set hereinbefore on the apparent velocity of each reaction material passing from the No.1 catalyst bed through the No.n catalyst bed.

According to this invention, as one way of changing the apparent velocity, there may be exemplified a way of gradually reducing the cross-sectional areas of the No.1 catalyst bed through the No.n catalyst bed so as to gradually increase the apparent velocity of each corresponding reaction material, so as to meet the requirements as set hereinbefore. For example if n represents 2, by changing the cross-sectional area of the No.2 catalyst bed to be smaller than that of the No.1 catalyst bed, it is possible to increase accordingly the apparent velocity of the reaction material passing through the No.2 catalyst bed, so as to meet the requirements as set hereinbefore. Specifically, if m represents any integer in the region [2, n], it is preferably to render $A_{m-1}/A_m>1$, preferably $A_{m-1}/A_m\geq 1.5$, more preferably $A_{m-1}/A_m\geq 2$. Further, if m represents any integer in the region [2, n], it is preferably to render $A_{m-1}/A_m\leq 15$, more preferably $A_{m-1}/A_m\leq 10$, further preferably $A_{m-1}/A_m\leq 5$. Herein, $A_{m-1}$ represents the averaged cross-sectional area of the No. m−1 catalyst bed, $A_m$ represents the averaged cross-sectional area of the No. m catalyst bed. According to an embodiment, the cross-section of each of the No.1 catalyst bed through the No.n catalyst bed has a circular shape, so that the averaged cross-sectional area can be simplified as averaged diameter. According to another embodiment, each of the No.1 catalyst bed through the No.n catalyst bed takes the cylindrical shape of fixed diameter, so that the averaged cross-sectional area can be simplified as diameter (of the cylindrical column).

According to this invention, as another way of changing the apparent velocity, there may be exemplified a way of introducing a carrier fluid into the compartment(s) (for example that as hereinbefore described) between any two or more pairs of adjacent catalyst beds among the No.1 catalyst bed through the No.n catalyst bed, so as to increase the overall throughput of the reaction material(s) passing through all of the catalyst beds located downstream from the compartment, whereby increasing accordingly the apparent velocity of each reaction material, so as to meet the requirements as set hereinbefore. For example, if n represents 2, by introducing a carrier fluid into the compartment between the No.1 catalyst bed and the No.2 catalyst bed, it is possible to increase the overall throughput of the reaction material passing through the No.2 catalyst bed, whereby increasing accordingly the apparent velocity of the reaction material passing through the No.2 catalyst bed, so as to meet the requirements as set hereinbefore.

According to the another way of changing the apparent velocity, as the carrier fluid, there may be exemplified any fluid that is capable of mixing with the reaction material coming from the catalyst bed located immediately upstream of the compartment and has substantially no unfavorably effect (for example reducing the activity) on any catalyst loaded in each catalyst bed located downstream from the compartment. As the carrier fluid, for example there may be exemplified the aforesaid reaction discharge, the aforesaid solvent, an inert gas and the aforesaid exhaust stream. As the inert gas, for example there may be exemplified nitrogen gas, Ar, and lower alkanes, wherein from the standpoint of rendering the olefin oxidation reaction more stable and economic, generally, it is preferably nitrogen gas. As the carrier fluid, it is more preferably the reaction discharge, the inert gas or a combination thereof at any ratio therebetween.

According to this invention, the carrier fluid is introduced merely for increasing the overall throughput of the reaction material(s) passing through all of the catalyst beds located downstream from compartment (hereinafter referred to as downstream catalyst bed), but not for taking part in the olefin oxidation reaction conducted in the downstream catalyst bed(s), and for this reason, the carrier fluid may happen to comprise a material capable of taking part in the olefin oxidation reaction conducted in the downstream catalyst bed(s) (for example any unreacted reactants), however, a material of this kind has been not intentionally introduced by this invention into the downstream catalyst bed(s), and the introduction of a material of this kind is believed as not responsible for the effect(s) to be obtained with this invention for the reason that the effect(s) can be obtained as well by the introduction of the solvent or the inert gas, which does not contain a material of this kind at all. For this reason, according to this invention, the carrier fluid is in no sense regarded as a reaction feed or a reaction raw material.

According the another way of changing the apparent velocity, there is no specific limitation on the amount and the way at which the carrier fluid is introduced, as long as (1) the carrier fluid is capable of before, during or after entering the catalyst bed located immediately downstream from the compartment, mixing till homogeneously with the reaction material coming from the catalyst bed located immediately upstream of the compartment, and (2) the apparent velocity of each reaction material meets the requirements as set hereinbefore. According to a specific embodiment, as aforesaid, the temperature of the carrier fluid is preferably lower than that of the reaction material coming from the catalyst bed located immediately upstream of the compartment (i.e. the reaction material immediately before entering the catalyst bed located immediately downstream from the compartment), whereby effectively reducing the reaction temperature in the downstream catalyst bed(s).

According to this invention, the aforesaid two ways of changing the apparent velocity may be used with one kind, or may be used in combination as needed.

This invention further relates to a fixed-bed reaction apparatus, which is specifically suitable for conducting the aforesaid olefin oxidation process of this invention, but not limiting thereto. Hereinafter, by referring to the figures, the fixed-bed reaction apparatus of this invention is described in more details. To simplify the specification, any item, embodiment or content described hereinbefore in connection with the olefin oxidation process is omitted, and hereinafter only item, embodiment or content specific to the fixed-bed reaction apparatus is described in more details.

According to this invention, the fixed-bed reaction apparatus comprises an entrance 1, a reaction zone 3 and an exit 2, wherein into the reaction zone 3 there are arranged the No.1 catalyst bed through the No.n catalyst bed, a reaction feed A from the entrance 1 enters the reaction zone 3, successively passes from the No.1 catalyst bed through the No.n catalyst bed, then flows out of the exit 2 as a reaction discharge B. In this connection, the fixed-bed reaction apparatus further comprises a speed-increasing means, such that if the apparent velocity of each of the reaction materials passing from the No.1 catalyst bed through the No.n catalyst bed is respectively named as $v_1$ to $v_n$, and if m represents any integer in the region [2, n], the relationship $v_{m-1}<v_m$ holds. Herein, each of the symbols and terms has the same meaning as hereinbefore defined.

According to this invention, as hereinbefore described, the No.1 catalyst bed through the No.n catalyst bed may be arranged into a single one reactor, constituting multiple reaction zones of the reactor, such that the reaction zone 3 corresponds to these multiple reaction zones of the reactor, or may each be arranged into n reactors respectively, constituting n multiple reactors, such that the reaction zone 3 corresponds to the multiple reactors, or may be arranged into two or more reactors in a combination, constituting a combination of multiple reaction zones and multiple reactors, such that the reaction zone 3 corresponds to the combination of multiple reaction zones and multiple reactors. In these situations, the entrance 1 and the exit 2 respectively correspond to the first entrance and the final exit of the fixed-bed reaction apparatus.

According to this invention, the speed-increasing means is introduced for gradually increasing the apparent velocity of each of the reaction materials passing from the No.1 catalyst bed through the No.n catalyst bed, so as to meet the requirements as set hereinbefore.

According to this invention, as the speed-increasing means, for example there may be exemplified a diameter-changing section of the reaction zone 3 and/or a reactor internal inside the reaction zone 3, wherein the diameter-changing section or the internal is so arranged that if m represents any integer in the region [2, n], the relationship $A_{m-1}/A_m>1$ holds. Herein, each of the symbols and terms has the same meaning as hereinbefore defined.

According to this invention, as the reactor internal (also referred to as internal) inside the reaction zone 3, for example there may be exemplified various members arranged into the multiple reaction zones of a single one reactor or those respectively arranged into multiple reactors, for reducing the original averaged cross-sectional area of the reaction zone or that of the reactor (whereby accordingly reducing the averaged cross-sectional area of the catalyst bed arranged in the reaction zone or reactor). As the internal, for example it may refer to those of FIG. 1 to FIG. 6. According to FIG. 1, the internal presents in the form of solid member of rectangular vertical section arranged along both sides of the No.2 catalyst bed II. The member of rectangular vertical section may extend around the periphery of the No.2 catalyst bed II, totally or partially surrounding the No.2 catalyst bed II. According to FIG. 2, the reactor internal has a maze-like vertical section, wherein the reaction material flows in a tortuous manner as indicated in the figure, and comes to the exit 2 from the bottom-right side of the maze. According to FIG. 3, the reactor internal presents in the form of solid cylindrical member arranged at the center of the No.2 catalyst bed II. According to FIG. 4, the reactor internal is arranged at the center of the No.2 catalyst bed II, and has a central cavity, with both left and right ends closed at the side approaching the exit 2, the reaction material flows into the cavity through holes on the wall thereof (5 holes in FIG. 4), and then flows to the exit 2. According to FIG. 5, the reactor internal presents in the form of solid hemisphere member arranged at the center of the No.2 catalyst bed II. According to FIG. 6, the reactor internal presents in the form of solid member of triangular vertical section arranged at both sides of the No.2 catalyst bed II. The member of triangular vertical section may extend around the periphery of the No.2 catalyst bed II, totally or partially surrounding the No.2 catalyst bed II.

Figure 7:
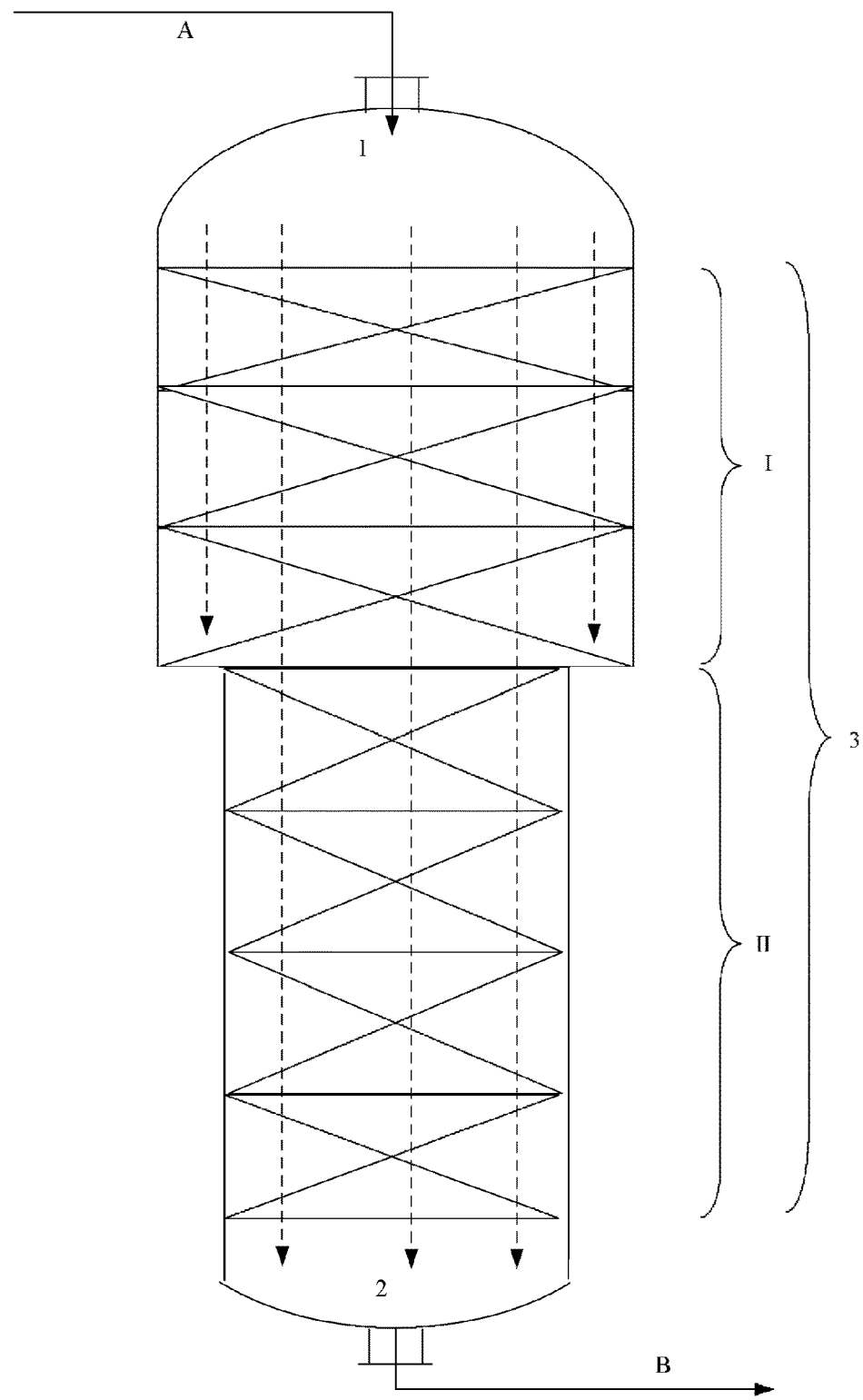
FIG. 7 illustrates an embodiment of the diameter-changing section.

According to this invention, as the diameter-changing section, for example there may be exemplified two or more reaction zones of different averaged cross-sectional area arranged into a single one reactor, two or more reactors of different averaged cross-sectional area or any combination thereof. As the two or more reaction zones of different averaged cross-sectional area in a single one reactor, for example it may refer to FIG. 7. According to FIG. 7, a cylindrical reactor has two reaction zones (upper and lower) of different averaged cross-sectional area or diameter, wherein into the upper reaction zone of greater diameter, there is arranged the No.1 catalyst bed I, and into the lower reaction zone of smaller diameter, there is arranged the No.2 catalyst bed II.

According to this invention, the speed-increasing means may also be a reaction discharge introduction conduit, wherein the reaction discharge introduction conduit introduces a part of the reaction discharge (as a carrier fluid) into a compartment between any two or more pairs of adjacent catalyst beds among the No.1 catalyst bed through the No.n catalyst bed. As the reaction discharge introduction conduit, for example it may refer to FIG. 8. According to FIG. 8, through the reaction discharge introduction conduits B1 to B4, a part of the reaction discharge B is introduced into a compartment between different catalyst beds (for example that between the No.1 catalyst bed I and the No.2 catalyst bed II, and that between the No.2 catalyst bed II and the No.3 catalyst bed III). By any way known in this field, a fluid distributor or the like can be arranged into the compartment, whereby facilitating an even introduction of the carrier fluid. If needed, before being introduced into the compartment, the carrier fluid may be subject to a pretreatment like heat-exchange (for example cooling) or pressurization.

This invention further relates to a system for olefin oxidation, which comprises at least a reaction feed unit, an olefin oxidation reaction unit and a reaction discharge separation unit.

According to this invention, those commonly known in this field for an olefin oxidation reaction are applicable to the reaction feed unit and the reaction discharge separation unit as such. For example, the reaction discharge separation unit isolates an olefin oxide from a reaction discharge of the fixed-bed reaction apparatus, to leave over an exhaust stream. Further, according to the present system for olefin oxidation, the olefin oxidation reaction unit comprises one or more of the fixed-bed reaction apparatus as hereinbefore described as the olefin oxidation reactor.

According to this invention, in the fixed-bed reaction apparatus, the speed-increasing means may also be an exhaust stream introduction conduit, and the exhaust stream introduction conduit introduces the exhaust stream or a part thereof (as a carrier fluid) into a compartment between any two or more pairs of adjacent catalyst beds among the No.1 catalyst bed through the No.n catalyst bed. As the exhaust stream introduction conduit, for example it may refer to FIG. 9. According to FIG. 9, through the exhaust stream introduction conduits C1 to C4, the exhaust stream C is introduced into a compartment between different catalyst beds (for example that between the No.1 catalyst bed I and the No.2 catalyst bed II, and that between the No.2 catalyst bed II and the No.3 catalyst bed III). By any way known in this field, a fluid distributor or the like can be arranged into the compartment, whereby facilitating an even introduction of the carrier fluid. If needed, before being introduced into the compartment, the carrier fluid may be subject to a pretreatment like heat-exchange (for example cooling) or pressurization. Further, one or more of the introduction conduits C1 to C4 may also be a solvent introduction conduit, an inert gas introduction conduit, a reaction discharge introduction conduit or any combination thereof, whereby at the same time or additionally introducing a solvent, an inert gas or the reaction discharge or any combination thereof into the compartment.

EXAMPLE

The following examples illustrate rather than limit this invention.

In the following examples and comparative examples, unless otherwise specified, the chemicals were all commercially available and analytically pure, the pressure was expressed as gauge pressure, and titanium silicalite was freshly produced.

In the following examples and comparative examples, the hollow titanium silicalite was produced in line with the process described in the Chinese patent CN1132699C, with a titania content of 2.5 wt %, the titanium silicalite TS-1 was produced in line with the process disclosed in *Journal of Natural Gas Chemistry*, 2001, 10(4):295-307, lines 9-24, page 296, with a titania content of 2.5 wt %, the titanium silicalite Ti-MCM-41 was produced in line with the process disclosed in *Chem. Commun.*, Corma et. al. 1994, pages 147-148, with a titania content of 3.0 wt %, the titanium silicalite Ti-Beta was produced in line with the process disclosed in *J. Chem. Soc. Chem. Commun.*, Takashi Tatsumi et. al. 1997, pages 677-678, with a titania content of 2.6 wt %.

In the following examples and comparative examples, the amount of each component in the product mixture was analyzed by gas chromatography, on the basis of which, the oxidant conversion, the oxidant utilization ratio, the selectivity to epoxide (as the aimed oxidation product), the selectivity to methyl formate (as a by-product) and the selectivity to acetone (as a by-product) were respectively calculated as follows:

The oxidant conversion=(the amount by molar of the oxidant consumed by the reaction/the amount by molar of the oxidant introduced into the reaction)×100%, The oxidant utilization ratio=(the amount by molar of the epoxide produced by the reaction/the amount by molar of the oxidant consumed by the reaction)×100%, The selectivity to epoxide=(the amount by molar of the epoxide produced by the reaction/the amount by molar of olefin consumed by the reaction)×100%, The selectivity to methyl formate=(the amount by molar of methyl formate produced by the reaction/the amount by molar of olefin consumed by the reaction)×1000000, The selectivity to acetone=(the amount by molar of acetone produced by the reaction/the amount by molar of olefin consumed by the reaction)× 1000000.

The following comparative examples and examples were provided for illustrating the process according to this invention.

In the examples and comparative examples, the molded hollow titanium silicalite (with a volume averaged particle size of 500 μm, and a density of 0.69 g/cm$^3$) comprises the hollow titanium silicalite and silica (as the binder), and based on the total amount of the molded hollow titanium silicalite, the amount of the hollow titanium silicalite was 75 wt %, the amount of silica was 25 wt %.

The molded titanium silicalite TS-1 (with a volume averaged particle size of 500 μm, and a density of 0.75 g/cm$^3$) comprises the titanium silicalite TS-1 and silica (as the binder), and based on the total amount of the molded titanium silicalite TS-1, the amount of the titanium silicalite TS-1 was 75 wt %, and the amount of silica was 25 wt %.

The molded titanium silicalite Ti-MCM-41 (with a volume averaged particle size of 500 μm, and a density of 0.63 g/cm$^3$) comprises the titanium silicalite Ti-MCM-41 and silica (as the binder), and based on the total amount of the molded titanium silicalite Ti-MCM-41, the amount of the titanium silicalite Ti-MCM-41 was 75 wt %, and the amount of silica was 25 wt %.

The molded titanium silicalite Ti-Beta (with a volume averaged particle size of 500 μm, and a density of 0.74 g/cm$^3$) comprises the titanium silicalite Ti-Beta and silica (as the binder), and based on the total amount of the molded titanium silicalite Ti-Beta, the amount of the titanium silicalite Ti-Beta was 75 wt %, and the amount of silica was 25 wt %.

Example 1

The reaction was carried out in two series-connected micro fixed-bed reactors, with each reactor provided with one catalyst bed of fixed diameter and round cross-section, and along the flowing direction of the reaction material, the ratio of the internal diameter of the No.1 catalyst bed in the first reactor located upstream to the internal diameter of the No.2 catalyst bed in the second reactor located downstream was 2:1, the No.1 catalyst bed was loaded with the molded hollow titanium silicalite, the No.2 catalyst bed was loaded with the molded titanium silicalite TS-1, the ratio by weight of the hollow titanium silicalite to the titanium silicalite TS-1 was 2:1.

Propylene, hydrogen peroxide as the oxidant (provided as a 30 wt % aqueous hydrogen peroxide solution) and methanol as the solvent were introduced from the bottom of the first reactor, made to pass through the No.1 catalyst bed to contact the molded hollow titanium silicalite loaded therein, discharged from the first reactor, then successively introduced into the second reactor, made to pass through the No.2 catalyst bed to contact the molded titanium silicalite TS-1 loaded therein.

Herein, the ratio by molar of propylene to hydrogen peroxide was 4:1, the ratio by weight of methanol to propylene was 10:1, the temperature in the No.1 catalyst bed and that in the No.2 catalyst bed were respectively 50 degrees Celsius, the pressure in the first reactor and that in the second reactor were respectively 2.8 MPa, based on the total amount of the titanium silicalites loaded in the No.1 catalyst bed and the No.2 catalyst bed, the weight space velocity of propylene was 2 h$^{-1}$.

The reaction was continuously carried out under the aforesaid conditions, during the reaction, the composition of the reaction product mixture discharged from the second reactor was analyzed, the oxidant conversion, the oxidant utilization ratio, the selectivity to propylene oxide, the selectivity to methyl formate and the selectivity to acetone were calculated, and the results obtained respectively at a reaction duration of 2 h and 860 h were listed in Table 1.

Example 2

The olefin oxidation was carried out in a manner similar to that of Example 1, with the exception that the molded titanium silicalite TS-1 in the No.2 catalyst bed was replaced by the molded hollow titanium silicalite of the same amount.

The results obtained respectively at a reaction duration of 2 h and 500 h were listed in Table 1.

Example 3

The olefin oxidation was carried out in a manner similar to that of Example 1, with the exception that the molded hollow titanium silicalite in the No.1 catalyst bed was replaced by the molded titanium silicalite TS-1 of the same amount.

The results obtained respectively at a reaction duration of 2 h and 480 h were listed in Table 1.

Example 4

The olefin oxidation was carried out in a manner similar to that of Example 1, with the exception that the molded titanium silicalite TS-1 in the No.2 catalyst bed was replaced by the molded titanium silicalite Ti-MCM-41 of the same amount.

The results obtained respectively at a reaction duration of 2 h and 600 h were listed in Table 1.

Example 5

The olefin oxidation was carried out in a manner similar to that of Example 4, with the exception that the molded hollow titanium silicalite in the No.1 catalyst bed was replaced by the molded titanium silicalite TS-1 of the same amount.

The results obtained respectively at a reaction duration of 2 h and 520 h were listed in Table 1.

Example 6

The olefin oxidation was carried out in a manner similar to that of Example 1, with the exception that with both the amount of the molded titanium silicalite TS-1 and the amount of the molded hollow titanium silicalite unchanged, the No.1 catalyst bed was loaded with the molded titanium silicalite TS-1, and the No.2 catalyst bed was loaded with the molded hollow titanium silicalite.

The results obtained respectively at a reaction duration of 2 h and 420 h were listed in Table 1.

Example 7

The olefin oxidation was carried out in a manner similar to that of Example 1, with the exception that the molded titanium silicalite TS-1 in the No.2 catalyst bed in the second reactor was replaced by the molded titanium silicalite Ti-Beta of the same amount.

The results obtained respectively at a reaction duration of 2 h and 580 h were listed in Table 1.

Example 8

The olefin oxidation was carried out in a manner similar to that of Example 1, with the exception that the reaction temperature of the No.1 catalyst bed and that of the No.2 catalyst bed were so adjusted that the reaction temperature of the No.1 catalyst bed was 50 degrees Celsius, and the reaction temperature of the No.2 catalyst bed was 35 degrees Celsius.

The results obtained respectively at a reaction duration of 2 h and 920 h were listed in Table 1.

Example 9

The olefin oxidation was carried out in a manner similar to that of Example 1, with the exception that the reaction temperature of the No.1 catalyst bed and that of the No.2 catalyst bed were so adjusted that the reaction temperature of the No.1 catalyst bed was 35 degrees Celsius, and the reaction temperature of the No.2 catalyst bed was 50 degrees Celsius.

The results obtained respectively at a reaction duration of 2 h and 800 h were listed in Table 1.

Example 10

The olefin oxidation was carried out in a manner similar to that of Example 1, with the exception that the reaction temperature of the No.1 catalyst bed and that of the No.2 catalyst bed were so adjusted that the reaction temperature of the No.1 catalyst bed was 50 degrees Celsius, and the reaction temperature of the No.2 catalyst bed was 65 degrees Celsius.

The results obtained respectively at a reaction duration of 2 h and 780 h were listed in Table 1.

Comparative Example 1

The olefin oxidation was carried out in a manner similar to that of Example 3, with the exception that with the nature and the amount of the catalyst loaded in the No.1 catalyst bed and those in the No.2 catalyst bed unchanged, the internal diameter of the No.2 catalyst bed was so increased that the ratio of the internal diameter of the No.1 catalyst bed to the internal diameter of the No.2 catalyst bed was 1:1. The results obtained respectively at a reaction duration of 2 h and 360 h were listed in Table 1.

Comparative Example 2

The olefin oxidation was carried out in a manner similar to that of Example 3, with the exception that with the nature and the amount of the catalyst loaded in the No.1 catalyst bed and those in the No.2 catalyst bed unchanged, the internal diameter of the No.2 catalyst bed was so increased that the ratio of the internal diameter of the No.1 catalyst bed to the internal diameter of the No.2 catalyst bed was 1:2. The results obtained respectively at a reaction duration of 2 h and 300 h were listed in Table 1.

TABLE 1

| No. | reaction duration (h) | oxidant conversion (%) | oxidant utilization ratio (%) | selectivity to propylene oxide (%) | selectivity to methyl formate (ppm) | selectivity to acetone (ppm) |
| --- | --- | --- | --- | --- | --- | --- |
| Example 1 | 2 | 99 | 91 | 98 | 205 | 62 |
|  | 860 | 92 | 84 | 90 | 164 | 55 |
| Example 2 | 2 | 99 | 89 | 97 | 341 | 191 |
|  | 500 | 86 | 80 | 87 | 224 | 178 |
| Example 3 | 2 | 97 | 88 | 95 | 354 | 185 |
|  | 480 | 87 | 79 | 86 | 226 | 174 |
| Example 4 | 2 | 96 | 86 | 92 | 412 | 268 |
|  | 600 | 86 | 77 | 83 | 392 | 264 |
| Example 5 | 2 | 94 | 85 | 92 | 545 | 292 |
|  | 520 | 85 | 76 | 83 | 521 | 279 |

TABLE 1-continued

| No. | reaction duration (h) | oxidant conversion (%) | oxidant utilization ratio (%) | selectivity to propylene oxide (%) | selectivity to methyl formate (ppm) | selectivity to acetone (ppm) |
|---|---|---|---|---|---|---|
| Example 6 | 2 | 98 | 90 | 93 | 472 | 264 |
|  | 420 | 88 | 81 | 84 | 443 | 234 |
| Example 7 | 2 | 96 | 86 | 94 | 243 | 138 |
|  | 580 | 86 | 77 | 85 | 216 | 132 |
| Example 8 | 2 | 99 | 93 | 98 | 92 | 22 |
|  | 920 | 91 | 86 | 90 | 54 | 45 |
| Example 9 | 2 | 96 | 90 | 96 | 261 | 155 |
|  | 800 | 88 | 81 | 86 | 235 | 144 |
| Example 10 | 2 | 99 | 89 | 90 | 209 | 326 |
|  | 780 | 94 | 78 | 73 | 185 | 459 |
| Comparative Example 1 | 2 | 97 | 88 | 95 | 508 | 152 |
|  | 360 | 82 | 75 | 80 | 566 | 181 |
| Comparative Example 2 | 2 | 95 | 87 | 95 | 469 | 197 |
|  | 300 | 80 | 74 | 80 | 547 | 245 |

As can be seen from a comparison of Example 3 with Comparative Examples 1 and 2, the process according to this invention is capable of effectively extending the single-pass service life of the titanium silicalite as the catalyst, lowering the frequency of catalyst regeneration, whereby improving the apparatus efficiency and reducing production cost.

As can be seen from a comparison of Example 1 with Examples 8 and 9, if the reaction temperature of the No.1 catalyst bed was set to be higher than that of the No.2 catalyst bed by a value of 5 to 30 degrees Celsius, it is possible to further increase the selectivity to epoxide, and further extend the single-pass service life of the catalyst.

Example 11

The molded hollow titanium silicalite (with a volume averaged particle size of 400 μm, and a density of 0.71 g/cm$^3$) to be used in this example comprises the hollow titanium silicalite and silica as the binder, and based on the total amount of the molded hollow titanium silicalite, the amount of the hollow titanium silicalite was 85 wt %, the amount of silica was 15 wt %.

The molded titanium silicalite TS-1 (with a volume averaged particle size of 400 μm, and a density of 0.77 g/cm$^3$) comprises the titanium silicalite TS-1 and silica as the binder, and based on the total amount of the molded titanium silicalite TS-1, the amount of the titanium silicalite TS-1 was 85 wt %, the amount of silica was 15 wt %.

The reaction was carried out in two series-connected micro fixed-bed reactors, with each reactor provided with one catalyst bed of fixed diameter and round cross-section, and along the flowing direction of the reaction material, the ratio of the averaged cross-sectional area of the No.1 catalyst bed in the first reactor located upstream to the averaged cross-sectional area of the No.2 catalyst bed in the second reactor located downstream was 5:1, the No.1 catalyst bed was loaded with the molded hollow titanium silicalite, the No.2 catalyst bed was loaded with the molded titanium silicalite TS-1, the ratio by weight of the hollow titanium silicalite to the titanium silicalite TS-1 was 10:1.

Propylene, hydrogen peroxide as the oxidant (provided as a 40 wt % aqueous hydrogen peroxide solution) and acetonitrile as the solvent were introduced from the bottom of the first reactor, made to pass through the No.1 catalyst bed to contact the molded hollow titanium silicalite loaded therein, discharged from the first reactor, then successively introduced into the second reactor, and made to pass through the No.2 catalyst bed to contact the molded titanium silicalite TS-1 loaded therein.

Herein, the ratio by molar of propylene to hydrogen peroxide was 2:1, the ratio by weight of acetonitrile to propylene was 10:1, the temperature in the No.1 catalyst bed and that in the No.2 catalyst bed were respectively 40 degrees Celsius, the pressure in the first reactor and that in the second reactor were respectively 2.0 MPa, based on the total amount of the titanium silicalite loaded in the No.1 catalyst bed and that in the No.2 catalyst bed, the weight space velocity of propylene was 6 h$^{-1}$.

The reaction was continuously carried out under the aforesaid conditions, during the reaction, the composition of the reaction product mixture discharged from the second reactor was analyzed, the oxidant conversion, the oxidant utilization ratio, the selectivity to propylene oxide, the selectivity to methyl formate and the selectivity to acetone were calculated, and the results obtained respectively at a reaction duration of 2 h and 900 h were listed in Table 2.

Example 12

The olefin oxidation was carried out in a manner similar to that of Example 11, with the exception that with the catalyst load in the No.1 catalyst bed and that in the No.2 catalyst bed unchanged, the internal diameter of the No.2 catalyst bed was so increased that the ratio of the averaged cross-sectional area of the No.1 catalyst bed to the averaged cross-sectional area of the No.2 catalyst bed was 2:1.

The results obtained respectively at a reaction duration of 2 h and 900 h were listed in Table 2.

Example 13

The olefin oxidation was carried out in a manner similar to that of Example 11, with the exception that with the catalyst load in the No.1 catalyst bed and that in the No.2 catalyst bed unchanged, the internal diameter of the No.1 catalyst bed was so increased that the ratio of the averaged cross-sectional area of the No.1 catalyst bed to the averaged cross-sectional area of the No.2 catalyst bed was 15:1.

The results obtained respectively at a reaction duration of 2 h and 860 h were listed in Table 2.

Example 14

The olefin oxidation was carried out in a manner similar to that of Example 11, with the exception that with the catalyst load in the No.1 catalyst bed and that in the No.2 catalyst bed unchanged, the internal diameter of the No.2 catalyst bed was so increased that the ratio of the averaged cross-sectional area of the No.1 catalyst bed to the averaged cross-sectional area of the No.2 catalyst bed was 3:2.

The results obtained respectively at a reaction duration of 2 h and 880 h were listed in Table 2.

Example 15

The olefin oxidation was carried out in a manner similar to that of Example 11, with the exception that the reaction temperature of the No.1 catalyst bed and that of the No.2 catalyst bed were so adjusted that the reaction temperature of the No.1 catalyst bed was 40 degrees Celsius, and the reaction temperature of the No.2 catalyst bed was 30 degrees Celsius.

The results obtained respectively at a reaction duration of 2 h and 920 h were listed in Table 2.

Example 16

The olefin oxidation was carried out in a manner similar to that of Example 11, with the exception that the reaction temperature of the No.1 catalyst bed and that of the No.2 catalyst bed were so adjusted that the reaction temperature of the No.1 catalyst bed was 30 degrees Celsius, and the reaction temperature of the No.2 catalyst bed was 40 degrees Celsius.

The results obtained respectively at a reaction duration of 2 h and 860 h were listed in Table 2.

Example 17

The olefin oxidation was carried out in a manner similar to that of Example 11, with the exception that the reaction temperature of the No.1 catalyst bed and that of the No.2 catalyst bed were so adjusted that the reaction temperature of the No.1 catalyst bed was 40 degrees Celsius, and the reaction temperature of the No.2 catalyst bed was 60 degrees Celsius.

The results obtained respectively at a reaction duration of 2 h and 820 h were listed in Table 2.

TABLE 2

| No. | reaction duration (h) | oxidant conversion (%) | oxidant utilization ratio (%) | selectivity to propylene oxide (%) | selectivity to methyl formate (ppm) | selectivity to acetone (ppm) |
|---|---|---|---|---|---|---|
| Example 11 | 2 | 98 | 92 | 96 | 261 | 82 |
|  | 900 | 90 | 85 | 86 | 225 | 71 |
| Example 12 | 2 | 97 | 91 | 96 | 141 | 53 |
|  | 900 | 88 | 83 | 87 | 124 | 48 |
| Example 13 | 2 | 98 | 90 | 95 | 404 | 266 |
|  | 860 | 88 | 81 | 86 | 386 | 261 |
| Example 14 | 2 | 98 | 90 | 96 | 426 | 224 |
|  | 880 | 85 | 81 | 86 | 348 | 187 |
| Example 15 | 2 | 98 | 94 | 97 | 105 | 22 |
|  | 920 | 90 | 86 | 89 | 92 | 11 |
| Example 16 | 2 | 96 | 91 | 94 | 331 | 152 |
|  | 860 | 86 | 82 | 85 | 284 | 140 |
| Example 17 | 2 | 99 | 90 | 91 | 250 | 327 |
|  | 820 | 95 | 79 | 83 | 196 | 452 |

Example 18

The molded hollow titanium silicalite (with a volume averaged particle size of 800 μm, and a density of 0.73 g/cm³) to be used in this example comprises the hollow titanium silicalite and silica as the binder, and based on the total amount of the molded hollow titanium silicalite, the amount of the hollow titanium silicalite was 80 wt %, the amount of silica was 20 wt %, The molded titanium silicalite TS-1 (with a volume averaged particle size of 800 μm, and a density of 0.78 g/cm³) to be used comprises the titanium silicalite TS-1 and silica as the binder, and based on the total amount of the molded titanium silicalite TS-1, the amount of the titanium silicalite TS-1 was 80 wt %, the amount of silica was 20 wt %.

The reaction was carried out in two series-connected micro fixed-bed reactors, with each reactor provided with one catalyst bed of fixed diameter and round cross-section, and along the flowing direction of the reaction material, the ratio of the averaged cross-sectional area of the No.1 catalyst bed in the first reactor located upstream to the averaged cross-sectional area of the No.2 catalyst bed in the second reactor located downstream was 4:1, the No.1 catalyst bed was loaded with the molded hollow titanium silicalite, the No.2 catalyst bed was loaded with the molded titanium silicalite TS-1, the ratio by weight of the hollow titanium silicalite to the titanium silicalite TS-1 was 6:1.

N-butene, tert-butyl hydroperoxide as the oxidant and tert-butanol as the solvent were introduced from the bottom of the first reactor, made to pass through the No.1 catalyst bed to contact the molded hollow titanium silicalite loaded therein, discharged from the first reactor, then successively introduced into the second reactor, and made to pass through the No.2 catalyst bed to contact the molded titanium silicalite TS-1 loaded therein.

Herein, the ratio by molar of n-butene to tert-butyl hydroperoxide was 1:1, the ratio by weight of tert-butanol to n-butene was 15:1, the temperature in the No.1 catalyst bed and that in the No.2 catalyst bed were respectively 40 degrees Celsius, the pressure in the first reactor and that in the second reactor were respectively 2.0 MPa, based on the total amount of the titanium silicalites loaded in the No.1 catalyst bed and in the No.2 catalyst bed, the weight space velocity of n-butene was 10 h$^{-1}$.

The reaction was continuously carried out under the aforesaid conditions, during the reaction, the composition of the reaction product mixture discharged from the second reactor was analyzed, the oxidant conversion, the oxidant utilization ratio, the selectivity to butylene oxide were calculated, and the results obtained respectively at a reaction duration of 2 h and 720 h were listed in Table 3.

TABLE 3

| No. | reaction duration (h) | oxidant conversion (%) | oxidant utilization ratio (%) | selectivity to butylene oxide (%) |
|---|---|---|---|---|
| Example 18 | 2 | 95 | 88 | 97 |
|  | 720 | 87 | 81 | 89 |

Example 19

The reaction was carried out in three series-connected micro fixed-bed reactors, with each reactor provided with one catalyst bed of fixed diameter and round cross-section, and along the flowing direction of the reaction material, the ratio between the averaged cross-sectional area of the No.1 catalyst bed in the first reactor located upstream, the averaged cross-sectional area of the No.2 catalyst bed in the second reactor located midstream and the averaged cross-sectional area of the No.3 catalyst bed in the third reactor located downstream was 4:2:1, and each catalyst bed was loaded with the molded hollow titanium silicalite.

Propylene, hydrogen peroxide as the oxidant (provided as a 30 wt % aqueous hydrogen peroxide solution) and methanol as the solvent was introduced from the bottom of the first reactor, made to pass through the No.1 catalyst bed to contact the molded hollow titanium silicalite loaded therein, discharged from the first reactor, then successively introduced into the second reactor, made to pass through the No.2 catalyst bed to contact the molded hollow titanium silicalite loaded therein, discharged from the second reactor, then successively introduced into the third reactor, made to pass through the No.3 catalyst bed to contact the molded hollow titanium silicalite loaded therein.

Herein, the ratio by molar of propylene to hydrogen peroxide was 3:1, the ratio by weight of methanol to propylene was 8:1, the temperature in the No.1 catalyst bed, that in the No.2 catalyst bed and that in the No.3 catalyst bed were respectively 45 degrees Celsius, the pressure in the first reactor, that in the second reactor and that in the third reactor were respectively 2.5 MPa, based on the total amount of the titanium silicalites loaded in the No.1 catalyst bed, in the No.2 catalyst bed and in the No.3 catalyst bed, and the weight hourly space velocity of propylene was 2 $h^{-1}$.

The reaction was continuously carried out under the aforesaid conditions, during the reaction, the composition of the reaction product mixture discharged from the third reactor was analyzed, the oxidant conversion, the oxidant utilization ratio, the selectivity to propylene oxide, the selectivity to methyl formate and the selectivity to acetone were calculated, and the results were listed in Table 4 hereinafter.

Comparative Example 3

The olefin oxidation reaction was carried out in line with the process according to Example 19, excepted that the three reactors had the same diameter, the averaged cross-sectional area of the catalyst bed in each reactor was the same as that of the No.1 catalyst bed, and the ratio of the catalyst load between these reactors was accordingly 1:1:1.

Example 20

The olefin oxidation reaction was carried out in line with the process according to Example 2, excepted that the reaction was carried out in one single reactor having two reaction zones of different diameter, which means that the two reactors of different diameter according to Example 2 were replaced by the two reaction zones of different diameter in one single reactor. Herein, the reactor having two reaction zones of different diameter was as specifically illustrated in FIG. 7, wherein the reaction material firstly contacted the reaction zone of larger internal diameter. In this example, the ratio of the averaged cross-sectional area between the two reaction zones was 2:1, and the ratio of the catalyst load between the two reaction zones was 2:1.

Comparative Example 4

The olefin oxidation reaction was carried out in line with the process according to Example 20, excepted that the reactor to be used herein was one single reactor having the same total length as that used in Example 20 and two reaction zones of the same diameter, wherein each cross-sectional area of the two reaction zones was the same as the cross-sectional area of the first reaction zone, and the ratio of the catalyst load between the two reaction zones was 1:1.

Example 21

The olefin oxidation reaction was carried out in line with the process according to Example 20, excepted that the reactor to be used was one single reactor having three reaction zones of different diameter, whose internal diameter gradually reduced, such that the reaction material firstly contacted the reaction zone of the largest internal diameter, wherein the ratio of the averaged cross-sectional area between the three reaction zones was 4:2:1, and the ratio of the catalyst load between the three reaction zones was 4:2:1.

Comparative Example 5

The olefin oxidation reaction was carried out in line with the process according to Example 21, excepted that the reactor to be used was one single reactor having the same total length as that of the reactor used in Example 21 and three reaction zones of the same diameter, wherein each cross-sectional area of the three reaction zones was the same as that of the first reaction zone in the reactor used in Example 21, and the ratio of the catalyst load between the three reaction zones was 1:1:1.

Example 22-27

The olefin oxidation reaction was carried out in line with the process according to Comparative Example 4, excepted that the second reaction zone in the reactor was respectively equipped with a reactor internal having a vertical section as illustrated in each of FIG. 1 to FIG. 6, whereby establishing two reaction zones of different diameter as respectively illustrated in each of FIG. 1 to FIG. 6, wherein the ratio of the averaged cross-sectional area between the two reaction zones was 2:1, and the ratio of the catalyst load between the two reaction zones was 2:1.

Example 28-33

The olefin oxidation reaction was carried out in line with the process according to Comparative Example 5, excepted that the third reaction zone in the reactor was respectively equipped with a reactor internal having a vertical section as illustrated in each of FIG. 1 to FIG. 6, whereby establishing three reaction zones of different diameter as respectively illustrated in each of FIG. 1 to FIG. 6, wherein the ratio of the averaged cross-sectional area between the three reaction zones was 2:2:1, and the ratio of the catalyst load between the three reaction zones was 2:2:1.

Example 34-39

The olefin oxidation reaction was carried out in line with the process according to each of Examples 22 to 27, excepted that the catalyst to be used was the same as that of Example 3, that is the molded titanium silicalite TS-1.

Comparative Example 6

The olefin oxidation reaction was carried out in line with the process according to Comparative Example 4, excepted that the catalyst to be used was the same as that of Example 3, that is the molded titanium silicalite TS-1.

Example 40-45

The olefin oxidation reaction was carried out in line with the process according to each of Examples 28 to 33, excepted that the catalyst to be used was the same as that of Example 3, that is the molded titanium silicalite TS-1.

Comparative Example 7

The olefin oxidation reaction was carried out in line with the process according to Comparative Example 5, excepted that the catalyst to be used was the same as that of Example 3, that is the molded titanium silicalite TS-1.

TABLE 4

| No. | reaction duration (h) | oxidant conversion (%) | oxidant utilization ratio (%) | selectivity to propylene oxide (%) | selectivity to methyl formate (ppm) | selectivity to acetone (ppm) |
|---|---|---|---|---|---|---|
| Example 19 | 2 | 100 | 93 | 99 | 188 | 59 |
|  | 720 | 94 | 89 | 94 | 143 | 41 |
| Comparative Example 3 | 2 | 99 | 89 | 93 | 197 | 149 |
|  | 400 | 86 | 83 | 86 | 249 | 177 |
| Example 20 | 2 | 100 | 91 | 98 | 224 | 78 |
|  | 720 | 89 | 88 | 92 | 207 | 55 |
| Comparative Example 4 | 2 | 98 | 90 | 94 | 296 | 143 |
|  | 400 | 87 | 84 | 88 | 379 | 168 |
| Example 21 | 2 | 100 | 93 | 98 | 211 | 163 |
|  | 720 | 92 | 90 | 94 | 202 | 141 |
| Comparative Example 5 | 2 | 98 | 88 | 93 | 284 | 155 |
|  | 400 | 83 | 81 | 86 | 361 | 196 |
| Example 22 | 2 | 97 | 91 | 96 | 195 | 65 |
|  | 720 | 87 | 86 | 94 | 175 | 51 |
| Example 23 | 2 | 98 | 92 | 97 | 228 | 79 |
|  | 720 | 86 | 88 | 91 | 204 | 65 |
| Example 24 | 2 | 99 | 92 | 97 | 255 | 58 |
|  | 720 | 89 | 88 | 92 | 229 | 47 |
| Example 25 | 2 | 97 | 92 | 95 | 224 | 75 |
|  | 720 | 90 | 89 | 93 | 199 | 59 |
| Example 26 | 2 | 97 | 92 | 96 | 175 | 107 |
|  | 720 | 92 | 88 | 91 | 137 | 85 |
| Example 27 | 2 | 97 | 92 | 97 | 244 | 72 |
|  | 720 | 89 | 89 | 92 | 218 | 41 |
| Example 28 | 2 | 98 | 92 | 98 | 187 | 49 |
|  | 720 | 88 | 87 | 96 | 167 | 45 |
| Example 29 | 2 | 99 | 92 | 99 | 223 | 73 |
|  | 720 | 87 | 89 | 93 | 196 | 52 |
| Example 30 | 2 | 98 | 93 | 99 | 247 | 85 |
|  | 720 | 90 | 89 | 94 | 221 | 71 |
| Example 31 | 2 | 98 | 93 | 97 | 216 | 69 |
|  | 720 | 91 | 90 | 95 | 191 | 53 |
| Example 32 | 2 | 98 | 93 | 98 | 167 | 91 |
|  | 720 | 93 | 89 | 93 | 129 | 86 |
| Example 33 | 2 | 98 | 93 | 99 | 236 | 83 |
|  | 720 | 90 | 90 | 94 | 212 | 55 |
| Example 34 | 2 | 96 | 91 | 95 | 199 | 124 |
|  | 720 | 86 | 84 | 91 | 179 | 117 |
| Example 35 | 2 | 97 | 92 | 96 | 232 | 145 |
|  | 720 | 85 | 85 | 90 | 208 | 132 |
| Example 36 | 2 | 98 | 92 | 96 | 259 | 117 |
|  | 720 | 88 | 86 | 91 | 233 | 93 |
| Example 37 | 2 | 96 | 92 | 94 | 228 | 84 |
|  | 720 | 89 | 85 | 90 | 203 | 75 |
| Example 38 | 2 | 96 | 92 | 95 | 179 | 93 |
|  | 720 | 91 | 86 | 90 | 141 | 98 |
| Example 39 | 2 | 96 | 92 | 96 | 248 | 108 |
|  | 720 | 88 | 86 | 89 | 222 | 97 |
| Comparative Example 6 | 2 | 96 | 91 | 95 | 359 | 146 |
|  | 400 | 83 | 82 | 87 | 396 | 173 |
| Example 40 | 2 | 97 | 91 | 97 | 195 | 118 |
|  | 720 | 87 | 86 | 95 | 171 | 102 |
| Example 41 | 2 | 98 | 91 | 98 | 227 | 139 |
|  | 720 | 86 | 88 | 92 | 200 | 125 |
| Example 42 | 2 | 97 | 92 | 98 | 251 | 118 |
|  | 720 | 89 | 88 | 93 | 225 | 87 |
| Example 43 | 2 | 97 | 92 | 96 | 220 | 85 |
|  | 720 | 90 | 89 | 94 | 195 | 79 |
| Example 44 | 2 | 97 | 92 | 97 | 171 | 87 |
|  | 720 | 92 | 88 | 92 | 133 | 92 |
| Example 45 | 2 | 97 | 92 | 98 | 240 | 102 |
|  | 720 | 89 | 89 | 93 | 216 | 95 |
| Comparative Example 7 | 2 | 97 | 88 | 94 | 288 | 121 |
|  | 400 | 82 | 81 | 87 | 333 | 146 |

Example 46

Figure 8:
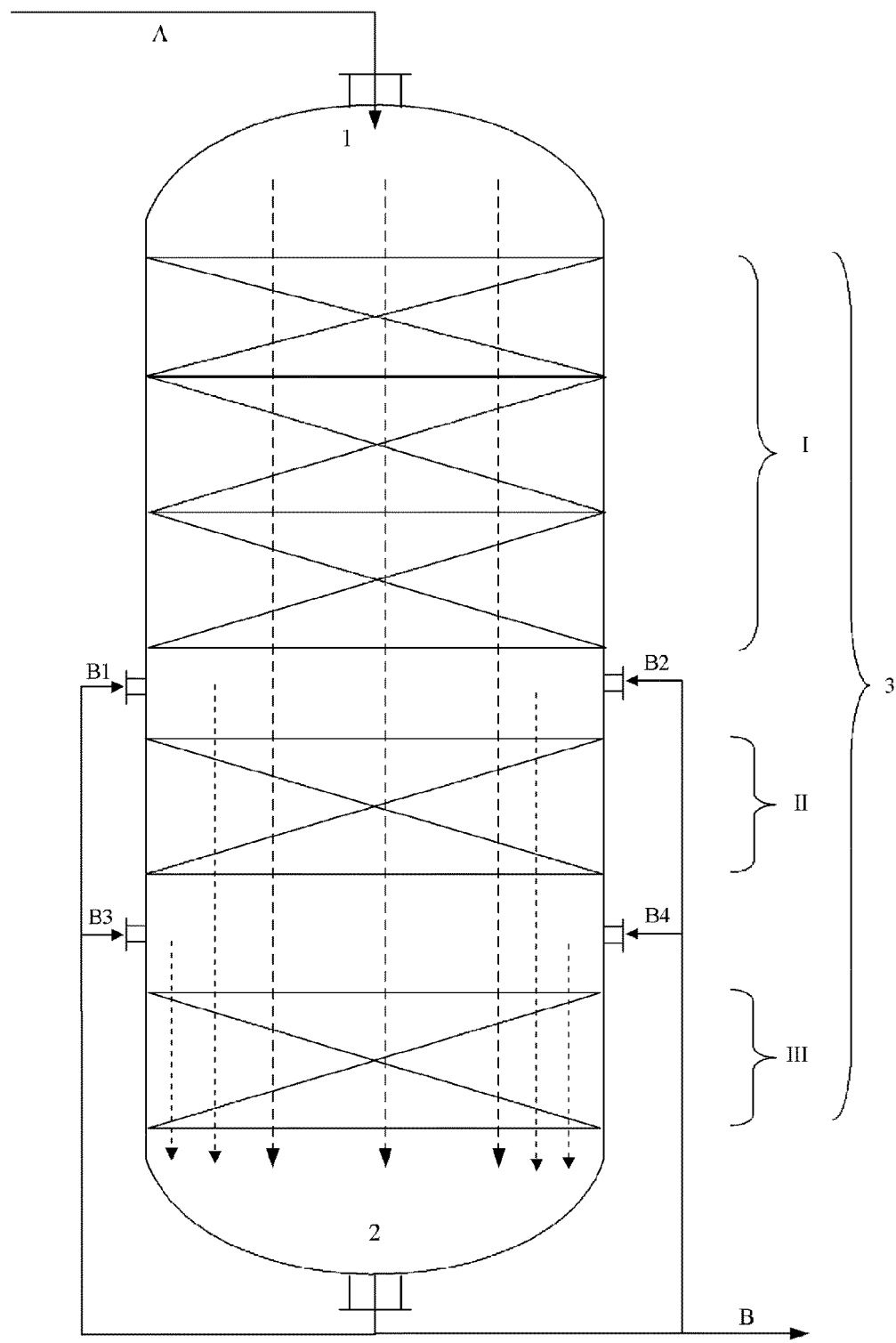
FIG. 8 illustrates an embodiment of the reaction discharge introduction conduit.

The olefin oxidation reaction was carried out in line with the process according to Comparative Example 4, wherein a part (with a percentage by mass of 20%) of the reaction discharge was evenly recycled to the compartment between the two reaction zones of fixed diameter in a manner as illustrated in FIG. 8 via two reaction discharge introduction conduits.

The reaction was continuously carried out under the aforesaid conditions, during the reaction, the composition of the reaction product mixture discharged from the reactor was analyzed, the oxidant conversion, the oxidant utilization ratio, the selectivity to propylene oxide, the selectivity to methyl formate and the selectivity to acetone were calculated, and hereinafter, the results were listed in Table 5.

Example 47

The olefin oxidation reaction was carried out in line with the process according to Example 20, wherein a part (with a percentage by mass of 20%) of the reaction discharge was evenly recycled to the compartment between the two reaction zones of different diameter in a manner as illustrated in FIG. 8 via two reaction discharge introduction conduits.

Example 48

The olefin oxidation reaction was carried out in line with the process according to Comparative Example 4, wherein a part (with a percentage by mass of 80%) of the reaction discharge was evenly recycled to the compartment between two reactors of fixed diameter (i.e. hereinafter, the two reactors corresponding to the two reaction zones in FIG. 8) in a manner as illustrated in FIG. 8 via two reaction discharge introduction conduits.

Example 49

The olefin oxidation reaction was carried out in line with the process according to Example 20, wherein a part (with a percentage by mass of 80%) of the reaction discharge was evenly recycled to the compartment between the two reactors of different diameter in a manner as illustrated in FIG. 8 via two reaction discharge introduction conduits.

Example 50

The olefin oxidation reaction was carried out in line with the process according to Comparative Example 3, wherein a part (with a percentage by mass of 20%) of the reaction discharge was evenly recycled to the compartments between the three reactors of fixed diameter in a manner as illustrated in FIG. 8 via four reaction discharge introduction conduits.

Example 51

The olefin oxidation reaction was carried out in line with the process according to Example 19, wherein a part (with a percentage by mass of 20%) of the reaction discharge was evenly recycled to the compartments between the three reactors of different diameter in a manner as illustrated in FIG. 8 via four reaction discharge introduction conduits.

Example 52

Figure 9:
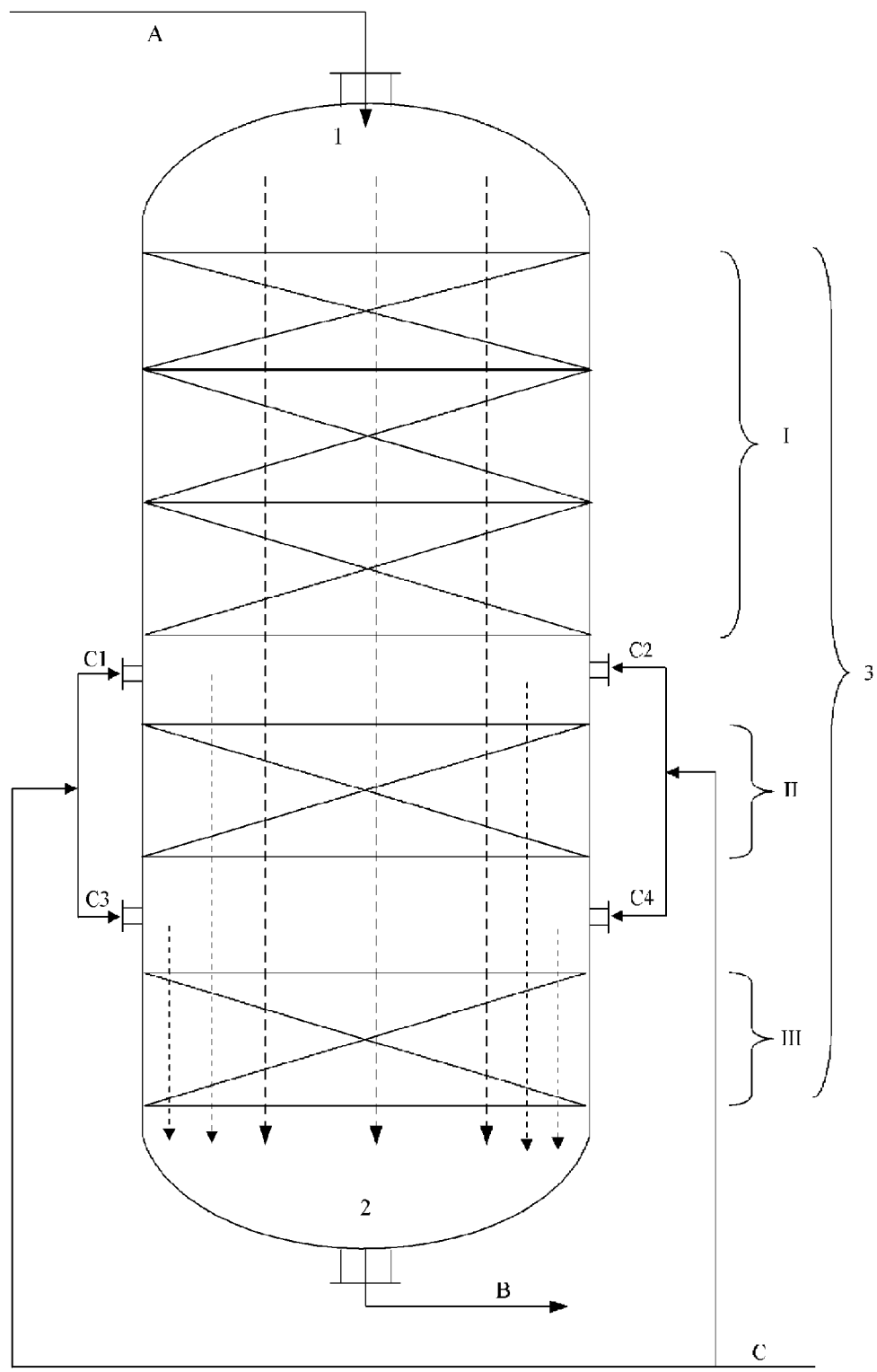
FIG. 9 illustrates an embodiment of the exhaust stream introduction conduit, the solvent introduction conduit or the inert gas introduction conduit.

The olefin oxidation reaction was carried out in line with the process according to Comparative Example 4, wherein a part (with a percentage by mass of 20%) of the solvent methanol was evenly introduced into the compartment between the two reaction zones of fixed diameter in a manner as illustrated in FIG. 9 via two solvent introduction conduits.

Example 53

The olefin oxidation reaction was carried out in line with the process according to Example 20, wherein a part (with a percentage by mass of 20%) of the solvent methanol was evenly introduced into the compartment between the two reaction zones of different diameter in a manner as illustrated in FIG. 9 via two solvent introduction conduits.

Example 54

The olefin oxidation reaction was carried out in line with the process according to Comparative Example 4, wherein a part (with a percentage by mass of 80%) of the solvent methanol was evenly introduced into the compartment between the two reactors of fixed diameter in a manner as illustrated in FIG. 9 via two solvent introduction conduits.

Example 55

The olefin oxidation reaction was carried out in line with the process according to Example 20, wherein a part (with a percentage by mass of 80%) of the solvent methanol was evenly introduced into the compartment between the two reactors of different diameter in a manner as illustrated in FIG. 9 via two solvent introduction conduits.

Example 56

The olefin oxidation reaction was carried out in line with the process according to Comparative Example 4, wherein nitrogen gas (as the carrier fluid, with an amount of 10% by weight relative to the total amount of the reaction material) was evenly introduced into the compartment between the two reaction zones of fixed diameter in a manner as illustrated in FIG. 9 via two inert gas introduction conduits.

Example 57

The olefin oxidation reaction was carried out in line with the process according to Example 20, wherein nitrogen gas (as the carrier fluid, with an amount of 10% by weight relative to the total amount of the reaction material) was evenly introduced into the compartment between the two reaction zones of different diameter in a manner as illustrated in FIG. 9 via two inert gas introduction conduits.

Example 58

The olefin oxidation reaction was carried out in line with the process according to Comparative Example 4, wherein nitrogen gas (as the carrier fluid, with an amount of 50% by weight relative to the total amount of the reaction material) was evenly introduced into the compartment between the two reactors of fixed diameter in a manner as illustrated in FIG. 9 via two inert gas introduction conduits.

Example 59

The olefin oxidation reaction was carried out in line with the process according to Example 20, wherein nitrogen gas (as the carrier fluid, with an amount of 50% by weight relative to the total amount of the reaction material) was evenly introduced into the compartment between the two reactors of different diameter in a manner as illustrated in FIG. 9 via two inert gas introduction conduits.

Example 60

The olefin oxidation reaction was carried out in line with the process according to Comparative Example 3, wherein nitrogen gas (as the carrier fluid, with an amount of 20% by weight relative to the total amount of the reaction material) was evenly introduced into the compartments between the three reactors of fixed diameter in a manner as illustrated in FIG. 9 via four inert gas introduction conduits.

Example 61

The olefin oxidation reaction was carried out in line with the process according to Example 19, wherein nitrogen gas (as the carrier fluid, with an amount of 20% by weight relative to the total amount of the reaction material) was evenly introduced into the compartments between the three reactors of different diameter in a manner as illustrated in FIG. 9 via four inert gas introduction conduits.

Example 62

The olefin oxidation reaction was carried out in line with the process according to Comparative Example 4, wherein a part (with a percentage by mass of 20%) of a solvent stream obtained by separating the reaction discharge was evenly introduced into the compartment between the two reaction zones of fixed diameter in a manner as illustrated in FIG. 9 via two solvent introduction conduits.

Example 63

The olefin oxidation reaction was carried out in line with the process according to Example 20, wherein a part (with a percentage by mass of 20%) of a solvent stream obtained by separating the reaction discharge was evenly introduced into the compartment between the two reaction zones of different diameter in a manner as illustrated in FIG. 9 via two solvent introduction conduits.

Example 64

The olefin oxidation reaction was carried out in line with the process according to Comparative Example 4, wherein a part (with a percentage by mass of 80%) of a solvent stream obtained by separating the reaction discharge was evenly introduced into the compartment between the two reactors of fixed diameter in a manner as illustrated in FIG. 9 via two solvent introduction conduits.

Example 65

The olefin oxidation reaction was carried out in line with the process according to Example 20, wherein a part (with a percentage by mass of 80%) of a solvent stream obtained by separating the reaction discharge was evenly introduced into the compartment between the two reactors of different diameter in a manner as illustrated in FIG. 9 via two solvent introduction conduits.

Example 66

The olefin oxidation reaction was carried out in line with the process according to Example 2, excepted that the ratio of the averaged cross-sectional area of the No.1 catalyst bed in the upstream first reactor to the averaged cross-sectional area of the No.2 catalyst bed in the downstream second reactor was changed to 2.5:1, and ratio of the catalyst load therebetween was accordingly 2.5:1.

Example 67

The olefin oxidation reaction was carried out in line with the process according to Example 2, excepted that the ratio of the averaged cross-sectional area of the No.1 catalyst bed in the upstream first reactor to the averaged cross-sectional area of the No.2 catalyst bed in the downstream second reactor was changed to 8:1, and ratio of the catalyst load therebetween was accordingly 8:1.

Example 68

The olefin oxidation reaction was carried out in line with the process according to Example 2, excepted that the ratio of the averaged cross-sectional area of the No.1 catalyst bed in the upstream first reactor to the averaged cross-sectional area of the No.2 catalyst bed in the downstream second reactor was changed to 12:1, and ratio of the catalyst load therebetween was accordingly 12:1.

Example 69

The olefin oxidation reaction was carried out in line with the process according to Example 2, excepted that the ratio of the averaged cross-sectional area of the No.1 catalyst bed in the upstream first reactor to the averaged cross-sectional area of the No.2 catalyst bed in the downstream second reactor was changed to 20:1, and ratio of the catalyst load therebetween was accordingly 20:1.

TABLE 5

| No. | reaction duration (h) | oxidant conversion (%) | oxidant utilization ratio (%) | selectivity to propylene oxide (%) | selectivity to methyl formate (ppm) | selectivity to acetone (ppm) |
|---|---|---|---|---|---|---|
| Example 46 | 2 | 98 | 90 | 95 | 221 | 116 |
|  | 720 | 90 | 86 | 92 | 274 | 138 |
| Example 47 | 2 | 97 | 91 | 96 | 149 | 145 |
|  | 720 | 93 | 89 | 92 | 132 | 122 |
| Example 48 | 2 | 98 | 90 | 93 | 242 | 152 |
|  | 720 | 94 | 85 | 91 | 271 | 135 |
| Example 49 | 2 | 97 | 90 | 95 | 142 | 166 |
|  | 720 | 94 | 86 | 90 | 119 | 147 |
| Example 50 | 2 | 98 | 90 | 94 | 176 | 156 |
|  | 720 | 87 | 83 | 89 | 144 | 125 |
| Example 51 | 2 | 97 | 93 | 95 | 133 | 85 |
|  | 720 | 92 | 89 | 91 | 108 | 48 |
| Example 52 | 2 | 99 | 91 | 97 | 166 | 83 |
|  | 860 | 90 | 87 | 94 | 159 | 95 |
| Example 53 | 2 | 99 | 92 | 98 | 124 | 72 |
|  | 860 | 93 | 90 | 95 | 107 | 59 |
| Example 54 | 2 | 96 | 91 | 95 | 177 | 76 |
|  | 860 | 94 | 88 | 91 | 156 | 71 |
| Example 55 | 2 | 97 | 91 | 97 | 137 | 33 |
|  | 860 | 95 | 90 | 92 | 114 | 14 |
| Example 56 | 2 | 99 | 90 | 98 | 151 | 70 |
|  | 920 | 91 | 86 | 95 | 144 | 82 |
| Example 57 | 2 | 99 | 91 | 98 | 109 | 59 |
|  | 920 | 94 | 90 | 94 | 92 | 46 |
| Example 58 | 2 | 97 | 90 | 96 | 135 | 63 |
|  | 920 | 95 | 87 | 94 | 111 | 58 |
| Example 59 | 2 | 99 | 90 | 98 | 82 | 26 |
|  | 920 | 96 | 89 | 96 | 59 | 15 |
| Example 60 | 2 | 99 | 88 | 95 | 161 | 143 |
|  | 920 | 88 | 81 | 90 | 129 | 112 |
| Example 61 | 2 | 98 | 91 | 96 | 118 | 72 |
|  | 920 | 93 | 87 | 92 | 93 | 35 |

TABLE 5-continued

| No. | reaction duration (h) | oxidant conversion (%) | oxidant utilization ratio (%) | selectivity to propylene oxide (%) | selectivity to methyl formate (ppm) | selectivity to acetone (ppm) |
|---|---|---|---|---|---|---|
| Example 62 | 2 | 97 | 90 | 96 | 177 | 89 |
|  | 720 | 89 | 86 | 93 | 170 | 81 |
| Example 63 | 2 | 98 | 91 | 97 | 135 | 78 |
|  | 720 | 92 | 89 | 94 | 118 | 65 |
| Example 64 | 2 | 95 | 90 | 94 | 188 | 82 |
|  | 720 | 92 | 88 | 90 | 167 | 77 |
| Example 65 | 2 | 96 | 90 | 96 | 148 | 42 |
|  | 720 | 94 | 89 | 92 | 127 | 25 |
| Example 66 | 2 | 99 | 93 | 98 | 174 | 58 |
|  | 920 | 94 | 89 | 92 | 151 | 26 |
| Example 67 | 2 | 98 | 92 | 96 | 191 | 98 |
|  | 920 | 92 | 88 | 90 | 165 | 76 |
| Example 68 | 2 | 97 | 92 | 96 | 249 | 104 |
|  | 920 | 90 | 82 | 84 | 222 | 87 |
| Example 69 | 2 | 96 | 90 | 94 | 337 | 175 |
|  | 920 | 87 | 80 | 81 | 293 | 168 |

We claim:

1. An olefin oxidation process, comprising a step of successively passing a reaction mixture comprising an olefin and at least one oxidant through n catalyst beds respectively designated as No.1 catalyst bed through No. n catalyst bed, wherein an apparent velocity of the reaction mixture at the No.1 catalyst bed through the No. n catalyst bed are respectively designated as $v_1$ to $v_n$, and $$v_{m-1} < v_m,$$

wherein n represents an integer in the range of from 2 to 50, and m represents an integer from 2 to n.

2. The process according to claim 1, wherein $$A_{m-1}/A_m > 1,$$

wherein $A_{m-1}$ represents an averaged cross-sectional area of the No. m−1 catalyst bed, $A_m$ represents an averaged cross-sectional area of the No. m catalyst bed.

3. The process according to claim 1, further comprising the step of obtaining a reaction discharge comprising an olefin oxide; and isolating the olefin oxide from the reaction discharge, wherein the reaction discharge depleted of the olefin oxide forms an exhaust stream.

4. The process according to claim 3, wherein a compartment is disposed between two adjacent catalyst beds among the n catalyst beds, further comprising introducing a carrier fluid into the compartment, wherein the carrier fluid is at least one selected from the group consisting of the reaction discharge, a solvent, an inert gas, and the exhaust stream.

5. The process according to claim 1, wherein each of the n catalyst beds are independently loaded with at least one titanium silicalite.

6. The process according to claim 1, wherein in the reaction feed, a molar ratio of the olefin to the at least one oxidant is 0.1-10:1, and a weight hourly space velocity of the olefin is 0.1-20 $h^{-1}$, based on a total amount of catalyst loaded in the n catalyst beds, wherein a reaction pressure (gauge) is 0-5 MPa, and a reaction temperature is 0-120 degrees Celsius.

7. The process according to claim 1, wherein $$T_{m-1} - T_m = 5 \text{ to } 30,$$

wherein $T_{m-1}$ represents reaction temperature (in degree Celsius) across the No. m−1 catalyst bed, and $T_m$ represents reaction temperature (in degree Celsius) across the No. m catalyst bed.

8. A fixed-bed reaction apparatus, comprising an entrance, a reaction zone, n catalyst beds designated as No. 1 catalyst bed through No. n catalyst bed arranged within the reaction zone, and an exit, wherein a reaction mixture enters the reaction zone via the entrance and successively passes through the n catalyst beds, and then discharges from the exit as a reaction discharge, wherein the fixed-bed reaction apparatus further comprises a speed-increasing means arranged in such a manner that, when the apparent velocity of the reaction mixture passing through each of the No. 1 catalyst bed through the No. n catalyst bed are respectively designated as $v_1$ to $v_n$, the following relationship holds, $$v_{m-1} < v_m,$$

wherein n represents an integer in the range of from 2 to 50, and m represents any integer from 2 to n.

9. The fixed-bed reaction apparatus according to claim 8, wherein the speed-increasing means is a diameter-changing section of the reaction zone and/or an internal arranged within the reaction zone, and the diameter-changing section or the internal is arranged in such a manner that the following relationship holds, $$A_{m-1}/A_m > 1,$$

wherein $A_{m-1}$ represents an averaged cross-sectional area of the No. m−1 catalyst bed, $A_m$ represents an averaged cross-sectional area of the No. m catalyst bed.

10. The fixed-bed reaction apparatus according to claim 8, wherein the speed-increasing means is a reaction discharge introduction conduit, a solvent introduction conduit, an inert gas introduction conduit or any combination thereof, wherein the reaction discharge introduction conduit is arranged to introduce a part of the reaction discharge into one or more compartments, the solvent introduction conduit is arranged to introduce a solvent into one or more compartments, and the inert gas introduction conduit is arranged to introduce an inert gas into one or more compartments, wherein each of the one or more compartments is located between two adjacent catalyst beds among the n catalyst beds.

11. A system for olefin oxidation, comprising at least a reaction feed unit, an olefin oxidation reaction unit, and a reaction discharge separation unit, wherein the olefin oxidation reaction unit comprises one or more fixed-bed reaction apparatuses according to claim 8.

12. The system according to claim 11, wherein the reaction discharge separation unit isolates an olefin oxide from the reaction discharge of the fixed-bed reaction apparatus to form an exhaust stream that is depleted of olefin oxide, and wherein the speed-increasing means is an exhaust stream introduction conduit arranged to introduce the exhaust stream or a part thereof into one or more compartments in the fixed-bed apparatus, wherein each of the one or more compartments is disposed between two adjacent catalyst beds among the n catalyst beds.

13. The fixed-bed reaction apparatus according to claim 8, wherein n represents 2, 3, 4, 5, 6, 7, 8, 9, 10, 11, 12, 13, 14, 15, 16, 17, 18, 19 or 20.

14. The fixed-bed reaction apparatus according to claim 8, wherein n represents 2, 3, 4, 5, 6, 7, 8, 9 or 10.

15. The fixed-bed reaction apparatus according to claim 8, wherein the speed-increasing means is arranged in such a manner that the following relationship holds:

$$v_m/v_{m-1} = 1.5 \text{ to } 15.$$

16. The fixed-bed reaction apparatus according to claim 8, wherein the speed-increasing means is arranged in such a manner that the following relationship holds:

$$v_m/v_{m-1} = 2 \text{ to } 10.$$

17. The fixed-bed reaction apparatus according to claim 9, wherein the diameter-changing section or the internal is arranged in such a manner that the following relationship holds:

$$1 < A_{m-1}/A_m \leq 15.$$

18. The fixed-bed reaction apparatus according to claim 9, wherein the diameter-changing section or the internal is arranged in such a manner that the following relationship holds:

$$1.5 \leq A_{m-1}/A_m \leq 10.$$

19. The process according to claim 1, wherein the olefin is at least one selected from $C_{3-6}$ α-olefins, and the at least one oxidant is at least one selected from the group consisting of hydrogen peroxide, organic peroxides, and peracids.

20. The process according to claim 1, wherein $v_m/v_{m-1} = 1.5$ to 15, wherein m represents an integer from 2 to n.

* * * * *